US012324759B2

(12) United States Patent
Teng et al.

(10) Patent No.: US 12,324,759 B2
(45) Date of Patent: Jun. 10, 2025

(54) BRACE FOR A BODY JOINT AND METHOD OF MANUFACTURING THEREOF

(71) Applicant: NANYANG TECHNOLOGICAL UNIVERSITY, Singapore (SG)

(72) Inventors: Seok Po Phillis Teng, Singapore (SG); Chor Hiong Tee, Singapore (SG); Pui Wah Kong, Singapore (SG); Anthony Bert, Singapore (SG); Kah Fai Leong, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 943 days.

(21) Appl. No.: 17/052,506

(22) PCT Filed: May 2, 2019

(86) PCT No.: PCT/SG2019/050247
§ 371 (c)(1),
(2) Date: Nov. 2, 2020

(87) PCT Pub. No.: WO2019/212417
PCT Pub. Date: Nov. 7, 2019

(65) Prior Publication Data
US 2021/0236319 A1  Aug. 5, 2021

(30) Foreign Application Priority Data
May 2, 2018  (SG) ............................ 10201803671X

(51) Int. Cl.
*A61F 5/01* (2006.01)
*B33Y 10/00* (2015.01)
*B33Y 80/00* (2015.01)

(52) U.S. Cl.
CPC ................ *A61F 5/01* (2013.01); *B33Y 10/00* (2014.12); *B33Y 80/00* (2014.12)

(58) Field of Classification Search
CPC ........ A61F 5/01; A61F 5/0111; A61F 5/0127; A61F 13/00; A61F 13/00008;
(Continued)

(56) References Cited

U.S. PATENT DOCUMENTS 5,265,445 A * 11/1993 Shytles .................. D04B 21/18
602/76
5,450,625 A * 9/1995 Hu ...................... A63B 71/1225
2/22
(Continued)

FOREIGN PATENT DOCUMENTS

EP   2 526 794 A1   11/2012
EP   3 045 152 A1    7/2016
(Continued)

OTHER PUBLICATIONS

Alfuth et al., "Biomechanical Comparison of 3 Ankle Braces With and Without Free Rotation in the Sagittal Plane," *Journal of Athletic Training* 49(5):608-616, 2014.
(Continued)

*Primary Examiner* — Ophelia A Hawthorne
*Assistant Examiner* — Gina McCarthy
(74) *Attorney, Agent, or Firm* — Seed IP Law Group LLP

(57) ABSTRACT

A brace including at least a first and second anchor regions; and a mechanical metamaterial region between the first anchor region and the second anchor region. The mechanical metamaterial region including a mesh structure having a two-stage elastic deformation profile, including a first stage which crossover to a second stage at a predetermined strain threshold along a main tension direction. The first stage of the elastic deformation profile may be of a higher compliance than the second stage of the elastic deformation profile. Also provided is a method of manufacturing the brace, comprising generating a three dimensional model of the
(Continued)

body joint and the at least two portions of the body: determining a functional range of motion of the body joint and a upper limit of the functional range of motion of the body joint based on motion measurement or motion analysis of said three dimensional model; configuring a three dimensional model of the brace; and fabricating the brace via additive manufacturing such as 3D printing based on the configured three dimensional model of the brace.

20 Claims, 10 Drawing Sheets

(58) Field of Classification Search
CPC .................. A61F 13/066; A61F 5/0106; A61F 2007/0225; A61F 5/0123; A61F 5/0109; Y10T 428/2476; Y10T 442/00; D03D 9/00; D03D 17/00; D04B 1/10; D04B 1/104; D04B 21/06; D04B 21/10; A41D 13/06; A41D 13/065; A41D 13/00; A41D 13/08
See application file for complete search history.

(56) References Cited

U.S. PATENT DOCUMENTS

| | | | | |
|---|---|---|---|---|
| 5,906,637 | A * | 5/1999 | Davis | A61F 5/0106 607/108 |
| 6,767,332 | B1 | 7/2004 | Pardue et al. | |
| 8,164,232 | B2 | 4/2012 | Kornbluh et al. | |
| 8,613,716 | B2 | 12/2013 | Summit et al. | |
| 8,641,654 | B2 | 2/2014 | Verkade et al. | |
| 10,864,101 | B2 * | 12/2020 | Ito | A61F 5/0109 |
| 2001/0056251 | A1 | 12/2001 | Peters | |
| 2003/0083602 | A1 * | 5/2003 | Haaland | A61F 5/0102 602/5 |
| 2008/0154164 | A1 * | 6/2008 | Sheehan | A61F 5/01 523/105 |
| 2012/0277649 | A1 | 11/2012 | Matsuo et al. | |
| 2017/0079827 | A1 | 3/2017 | Ostergard | |
| 2017/0297278 | A1 * | 10/2017 | LeCursi | B29C 70/28 |
| 2018/0133045 | A1 * | 5/2018 | Ito | A61F 5/01 |
| 2018/0357348 | A1 * | 12/2018 | Veiga Rivero | A61F 5/05866 |

FOREIGN PATENT DOCUMENTS

| | | |
|---|---|---|
| EP | 3 287 027 A1 | 2/2018 |
| WO | 99/09917 A1 | 3/1999 |
| WO | 2005/089176 A2 | 9/2005 |

OTHER PUBLICATIONS

Feger et al., "Effect of Ankle Braces on Lower Extremity Muscle Activation During Functional Exercises in Participants with Chronic Ankle Instability," *The International Journal of Sports Physical Therapy* 9(4):476-487, 2014.

Fitzpatrick et al., "Design of a Patient Specific, 3D printed Arm Cast," *The International Conference on Design and Technology 2017*:135-142, 2017.

International Search Report and Written Opinion for International Application No. PCT/SG2019/050247, mailed Jul. 4, 2019, 12 pages.

Ion et al., "Metamaterial Mechanisms," *UIST '16*, Oct. 16-19, 2016, Tokyo, Japan, pp. 529-539.

Parsley et al., "Effect of 3 Different Ankle Braces on Functional Performance and Ankle Range of Motion," *Athletic Training & Sports Health Care* 5(2):69-75, 2013. (8 pages).

Teng et al., "The use of rapid prototyping in the design of a customised ankle brace structure for ACL injury risk reduction," *Virtual and Physical Prototyping* 8(4):241-247, 2013 (7 pages).

Zadpoor, "Mechanical meta-materials," *Mater. Horiz.* 3(5):371-381, 2016 (12 pages).

* cited by examiner

BRACE FOR A BODY JOINT AND METHOD OF MANUFACTURING THEREOF

CROSS-REFERENCE TO RELATED APPLICATIONS

The present application claims the benefit of the Singapore patent application Ser. No. 10201803671X filed on 2 May 2018, the entire contents of which are incorporated herein by reference for all purposes.

TECHNICAL FIELD

Various embodiments generally relate to a brace for a body joint between at least two portions of a body, and a method of manufacturing a brace for a body joint between at least two portions of a body.

BACKGROUND

Prophylactic braces have typically been used to prevent injuries such as at the elbows, knees and ankles. However, braces often limit range of motion, or are typically rigid and may thus result in discomfort after prolonged use. For example, ankle braces are common prophylactic braces to reduce ankle injury risks. These ankle braces fit into shoes and are configured to prevent excessive motion that may lead to the ankle sprain. However, in doing so, ankle braces could restrict the normal functional range of motion of the ankle. This in turn leads to restrictive play and could result in absorption of higher landing forces. This also reduces muscle activity and may result in long-term weakening of the muscles. Furthermore, these braces are often made of standard sizes and cutting which may not always fit nicely on a user.

Accordingly, there is a need for a more effective brace to address the above issues.

SUMMARY

According to various embodiments, there is provided a brace for a body joint between at least two portions of a body. The brace may include at least two anchor regions, wherein a first of the at least two anchor regions is configured to hold the brace to a first of the at least two portions of the body, and a second of the at least two anchor regions is configured to hold the brace to a second of the at least two portions of the body; and a mechanical metamaterial region between the at least two anchor regions, the mechanical metamaterial region including a mesh structure configured to have a two-stage elastic deformation profile along a main tension direction. According to various embodiments, the two-stage elastic deformation profile may include a first stage which crossover to a second stage at a predetermined strain threshold of the mesh structure. According to various embodiments, the first stage of the elastic deformation profile may be of a higher compliance than the second stage of the elastic deformation profile.

According to various embodiments, there is provided a method of manufacturing a brace for a body joint between at least two portions of a body. The method may include generating a three dimensional model of the body joint and the at least two portions of the body. The method may further include determining a functional range of motion of the body joint and a upper limit of the functional range of motion of the body joint based on motion measurement or motion analysis of the three dimensional model of the body joint and the at least two portions of the body. The method may further include configuring a three dimensional model of the brace as described herein in a manner so as to match the predetermined strain threshold of the mesh structure of the mechanical metamaterial region to the upper limit of the functional range of motion of the body joint such that the mesh structure is operating in the first stage of elastic deformation of the mesh structure within the functional range of motion of the body joint and the mesh structure is operating in the second stage of elastic deformation of the mesh structure beyond the upper limit of the functional range of motion of the body joint. The method may further include fabricating the brace via additive manufacturing based on the configured three dimensional model of the brace.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DETAILED DESCRIPTION

Figure 1A:
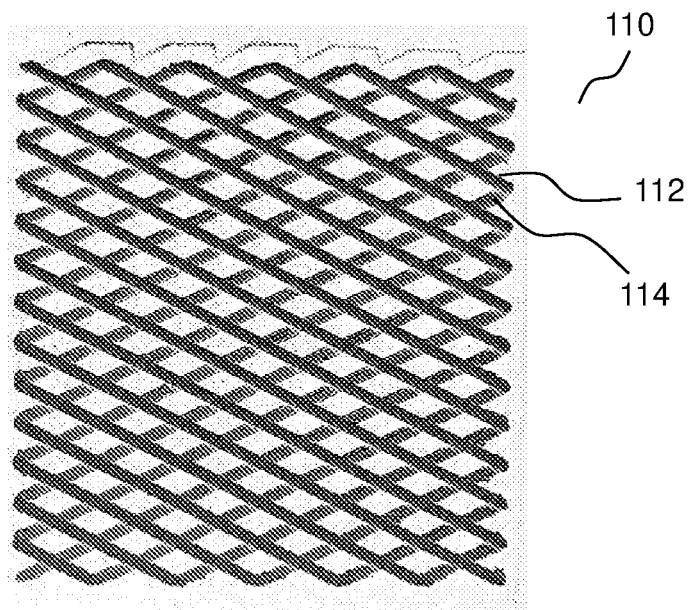
FIG. 1A shows an example of a mechanical metamaterial structure for a brace according to various embodiments.

Embodiments described below in the context of the apparatus are analogously valid for the respective methods, and vice versa. Furthermore, it will be understood that the embodiments described below may be combined, for example, a part of one embodiment may be combined with a part of another embodiment.

It should be understood that the terms "on", "over", "top", "bottom", "down", "side", "back", "left", "right", "front", "lateral", "side", "up", "down" etc., when used in the following description are used for convenience and to aid understanding of relative positions or directions, and not intended to limit the orientation of any device, or structure or any part of any device or structure. In addition, the singular terms "a", "an", and "the" include plural references unless context clearly indicates otherwise. Similarly, the word "or" is intended to include "and" unless the context clearly indicates otherwise.

Various embodiments generally relate to a brace (or a support brace) for a body joint between at least two portions of a body (e.g. a first body portion and a second body portion), and a method of manufacturing a brace (or a support brace) for a body joint between at least two portions of a body (e.g. a first body portion and a second body portion). In particular, various embodiments may relate to a customizable brace (or a customizable support brace) and a method of manufacturing a customizable brace (or a customizable support brace). According to various embodiments, the brace or the customizable brace may include anything that is worn on the body for the purpose of protection or support of the body part such as to reduce injury risks or to allow the body part to heal. According to various embodiments, the brace or the customizable brace may include standalone products such as prophylactic braces for body joints including, but not limited to, an ankle or an elbow or a knee or a wrist or a neck or a shoulder or a finger, or may be part of existing products such as textiles or shoes.

Various embodiments may relate to configuring of the customized brace (or support) products (e.g. an ankle support, a knee support, an elbow support, a wrist support, a neck support, a shoulder support etc.) that may be customized to the individual users. According to various embodiments, the brace (or the support brace) may be lightweight and breathable. Hence, the brace may be comfortable to the user when worn on the body over prolong periods of time. According to various embodiments, depending on the mobility requirements, clinicians may alter and customize the brace according to the individual needs (e.g. If mobility is to be restricted to aid initial healing, the brace may be configured to be rigid and non-stretchable. On the other hand, if the brace is to be utilized as a support brace to prevent injury, maximum mobility may be provided with the brace configured to restrict movement beyond the normal mobility range.)

Various embodiments may relate to a brace (or a support brace) for a user body or joint. The brace may also be incorporated as part of a textile or garment to be worn. According to various embodiments, the braces may be configured with mechanical metamaterial structures (or be based on a meta-structure body), that may be formed and customized to the body joint. According to various embodiments, the brace may have a mechanical metamaterial structure (or a meta-structure body) configured with selective regions having different mechanical properties. According to various embodiments, the brace may be configured to provide unrestrictive body joint kinematics motion within the full functional range of motion; and configured to restrict or prevent motion that is beyond the full functional range of motion (or range of motion) or beyond stipulated positions which may, for example, cause body joint injury. According to various embodiments, the range of motion may be customizable according to the requirements.

According to various embodiments, for fabrication, the brace or the customizable brace may be constructed based on the following:
a) Collecting relevant body part data, for example, using a three-dimensional (3D) scanner to scan and generating a 3D Computer-Aided Design (CAD) model of the user body joint;
b) Identifying body joint movement based on the body joint kinematics motion and generating the brace with a mechanical metamaterial structure (or a meta-structure) that allows unrestrictive motion for the body joint within the joint's functional range of motion and configuring the mechanical metamaterial structure to provide support and/or restricted motion to the body joint beyond the joint's functional range of motion or a range of motion that is associated with higher injury risks (or configuring the mechanical metamaterial structure to provide support and/or restricted motion to the body joint only at positions beyond the joint's functional range of motion or at positions that are, for example, associated with higher injury risks);
c) Using the 3D CAD model of the user body joint to construct a corresponding surface model for the body joint;
d) Fabricating the brace or the customizable brace using a 3D printing device.

Various embodiments relate to a customizable 'active' body brace (or smart brace) that is configured with mechanical metamaterial structures. Various embodiments may use mechanical metamaterial structures and soft, elastic materials to create the customizable 'active' body brace. According to various embodiments, the mechanical metamaterial structures may be made up of repeatedly arranged geometric structures. According to various embodiments, the mechanical metamaterial structures may include mesh-like structures. According to various embodiments, properties of the mechanical metamaterial structures may be determined by its configurations, for example shapes and/or dimensions and/or orientations and/or repeating patterns etc., of the geometric structures. According to various embodiments, the geometric structures may include symmetrical geometric structures and/or asymmetrical geometric structures. According to various embodiments, the geometric structures may be 3D printed in different orientations, with or without the use of textile, at different parts of the brace. According to various embodiments, customized positioning of the geometric structures may be possible with 3D printing, to provide customized protection or support based on each user's (or individual's) needs. According to various embodiments, the brace may allow full functional range of motion, but may slow down the joint motion at stipulated positions (or high risk positions), for example those associated with increased injury risks. According to various embodiments, with customized protection or support, while allowing freedom of movement within the functional range of motion, the brace may be used by, for example, sport players to reduce injury risks during sport activities. Although the example as described herein relates to prophylactic braces for reducing injury risks, various embodiments may also be used in other applications such as during different stages of rehabilitation or for customized elderly use.

According to various embodiments, the brace may be customized for each user's (or individual's) range of motion and body profile. According to various embodiments, the brace may allow the full functional range of motion required for activity or sport, and yet may provide protection by preventing the joint from going into extreme positions outside the functional range of motion, which are associated with higher injury risks. According to various embodiments, the brace may not restrict functional range of motion and may be customized for the individuals. According to various embodiments, the brace may be comfortable to be worn and may be free of rigid plastic parts that restrict joint motion.

According to various embodiments, the brace may be lightweight. According to various embodiments, the material may be soft, unlike semi-rigid plastic braces, and may therefore be more comfortable to wear for prolonged hours. According to various embodiments, the mechanical metamaterial structures may include mesh-like structures with gaps or holes which may also provide breathability of the material. According to various embodiments, any 3D printable elastic material may be used for the fabrication of the brace.

According to various embodiments, the brace may include the mechanical metamaterial structure. According to various embodiments, the mechanical metamaterial structure may form the basic structure of the brace. According to various embodiments, with the use of 3D printing, the metamaterial structure may be configured and printed. According to various embodiments, the mechanical metamaterial structure may be printed using elastic polymer and may include geometric structures such as diamonds or triangles or other suitable polygon shapes or other curvilinear shapes. According to various embodiments, other types of metamaterial structures may also be applicable. According to various embodiments, the mechanical metamaterial structure may optionally be printed on a stretchable support such as a fabric (or an elastic fabric). According to various embodiments, the fabric may provide comfort to the user and may also act as a base material or substrate which the mechanical metamaterial structure may be printed on.

According to various embodiments, the mechanical metamaterial structure may include a diamond mesh pattern, which is similar to the foam mesh packaging used for fruits. According to various embodiments, the mechanical metamaterial structure may include other suitable polygon shaped mesh pattern or curvilinear shaped mesh pattern. According to various embodiments, the mechanical metamaterial structure may be customizable. According to various embodiments, the mechanical metamaterial structure may include different region of mesh patterns that has different mechanical properties. In comparison, the traditional manufacturing method for foam mesh packaging is using double extrusion, which does not allow easy customization and is difficult to create different regions of metamaterial structures (or meta-structures) that has different mechanical properties.

According to various embodiments, the mechanical metamaterial structure may include a mesh structure having a plurality of links and nodes forming repeating shapes, for example polygon shapes such as diamond, triangle, rhombus, parallelogram, kite, pentagon, hexagon, honeycomb, octagon, etc., or curvilinear shapes such as ellipse, oval, circular, etc., According to various embodiments, when the mesh structure includes polygon shapes, each of the plurality of links may include a straight link. According to various embodiments, when the mesh structure includes curvilinear shapes, each of the plurality of links may include a curved link. According to various embodiments, each node may fixedly connect two or more links. According to various embodiments, each link may be configured to be capable of pivoting or flexing about respective node. According to various embodiments, each link may be configured to be elastically deformable in respective axial direction. In an initial stage of stretching the mechanical metamaterial structure, the plurality of links may be pivoted or flexed about corresponding nodes in a manner so as to compress or flatten the shapes (i.e. the polygon shapes or the curvilinear shapes) of the mesh structure in a direction perpendicular to the direction of stretching so as to straighten the shapes, and lengthen or elongate the shapes of the mesh structure in the direction of stretching. After the plurality of links is fully pivoted or flexed, subsequent stage of stretching of the mechanical metamaterial structure may require axial deformation of the respective links which requires a larger force than the force required to pivot or flex the plurality of links for a same amount of stretching.

According to various embodiments, multi-layer 3D printing may be done to form the mechanical metamaterial structure, with an upper layer material pattern printed over a lower layer material pattern, and with pivot points or flexing points (i.e. the contact point where the upper thread-like structure of the upper layer material pattern touches the adjacent thread-like structures of the lower layer material pattern) in the structure. Accordingly, the upper layer material pattern may pivot or flex about the lower layer material pattern which may allow the mechanical metamaterial structure to stretch more easily. According to various embodiments, by pivoting or flexing the upper layer material pattern with respect to the lower layer material pattern, the mesh pattern may become elongated and straightened so as to result in an extension of the mechanical metamaterial structure. When the mesh pattern is fully elongated and straightened, further stretching of the mechanical metamaterial structure may require axial deformation of the links of the mechanical metamaterial structure which needs more force as compared to pivoting or flexing the respective links.

Figure 1B:
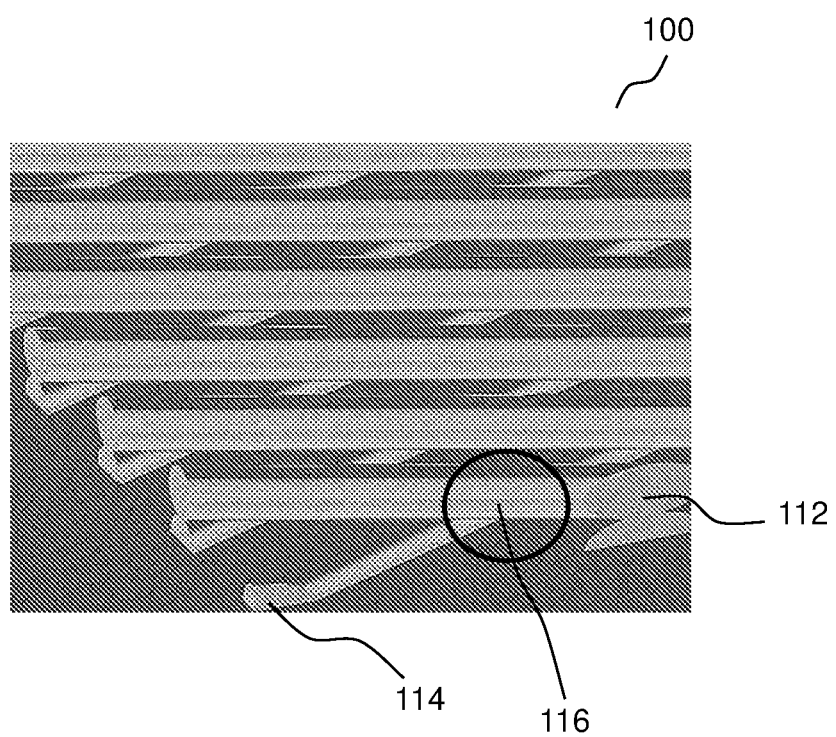
FIG. 1B shows a closed up view of a section of the mechanical metamaterial structure of FIG. 1A according to various embodiments.

FIG. 1A shows an example of a mechanical metamaterial structure 110 for a brace according to various embodiments. FIG. 1A shows the mechanical metamaterial structure 110 in the form of a diamond mesh structure by way of an illustration and not limitation. It is understood that the mechanical metamaterial structure 110 of the brace may include other mesh structure, for example other polygon shaped mesh structure or curvilinear shaped mesh structure. As shown in FIG. 1A, according to various embodiments, a top layer 112 (or the upper layer material pattern) may be printed on top of a bottom layer 114 (or the lower layer material pattern). FIG. 1B shows a closed up view of a section of the mechanical metamaterial structure 110 of FIG. 1A according to various embodiments. An example of the pivot point 116 of the mechanical metamaterial structure 110 is circled in FIG. 1B.

Figure 2:
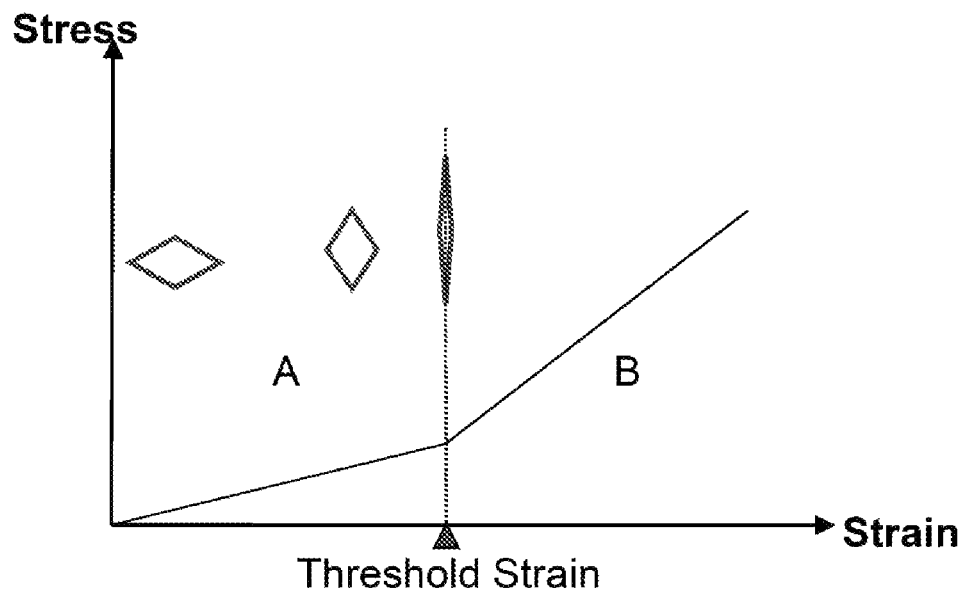
FIG. 2 shows a theoretical stress-strain curve in a stretching direction of the mechanical metamaterial structure of FIG. 1A according to various embodiments.

FIG. 2 shows a theoretical stress-strain curve in a stretching direction (shown in FIG. 3A as direction A) of the mechanical metamaterial structure 110 of FIG. 1A according to various embodiments. As shown, in the stretching direction, the diamond mesh structure of the mechanical metamaterial structure 110 may initially stretch easily (i.e. high deformation and low force), flexing the respective diamond structures (see Zone A in FIG. 2) until the diamond structures become fully elongated and straightened, which correspond to a threshold strain. After which, more force may be required to further stretch the diamond structures (see Zone B in FIG. 2) because the links of the respective diamond structures have to undergo axial deformation. According to various embodiments, the diamond mesh structure may have a two-stage elastic deformation profile along the stretching direction as shown by Zone A and Zone B in FIG. 2. According to various embodiments, Zone A (or a first stage) may crossover to Zone B (or a second stage) at a predetermined strain threshold of the diamond mesh structure. According to various embodiments, as shown in the stress-strain curve of FIG. 2, the diamond mesh structure may exhibit linear elastic deformation characteristic in both Zone A (the first stage) and Zone B (the second stage), and the elastic modulus in Zone B (the second stage) may be higher than that in Zone A (the first stage). According to various embodiments, Zone A (the first stage) may have a higher compliance or lower stiffness than Zone B (the second stage).

According to various embodiments, the mechanical metamaterial may include symmetrical shaped (or symmetrical polygon shaped or symmetrical curvilinear shaped) mesh patterns. According to various embodiments, the mechanical metamaterial structure may include asymmetrical shaped (or asymmetrical polygon shaped or asymmetrical curvilinear shaped) mesh patterns so as to be configured to provide anisotropic material properties. According to various embodiments, the mechanical metamaterial structure may be configured to have customized mechanical properties in different regions and/or directions. According to various embodiments, the mechanical properties of the mechanical metamaterial structure may be influenced by parameters such as type of geometric shape, size of geometric shape and thickness of shape. By varying these parameters, the mechanical metamaterial structure may be configured to have the desired properties.

Figure 3A:
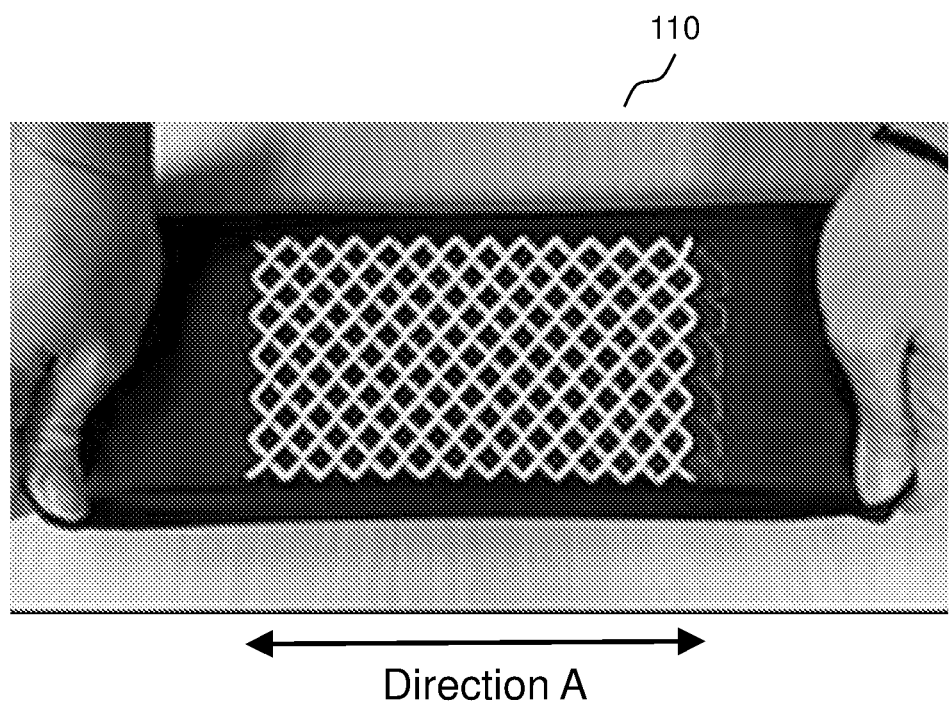
FIG. 3A and FIG. 3B show the mechanical metamaterial structure of FIG. 1A being stretched in different directions according to various embodiments.
Figure 3B:
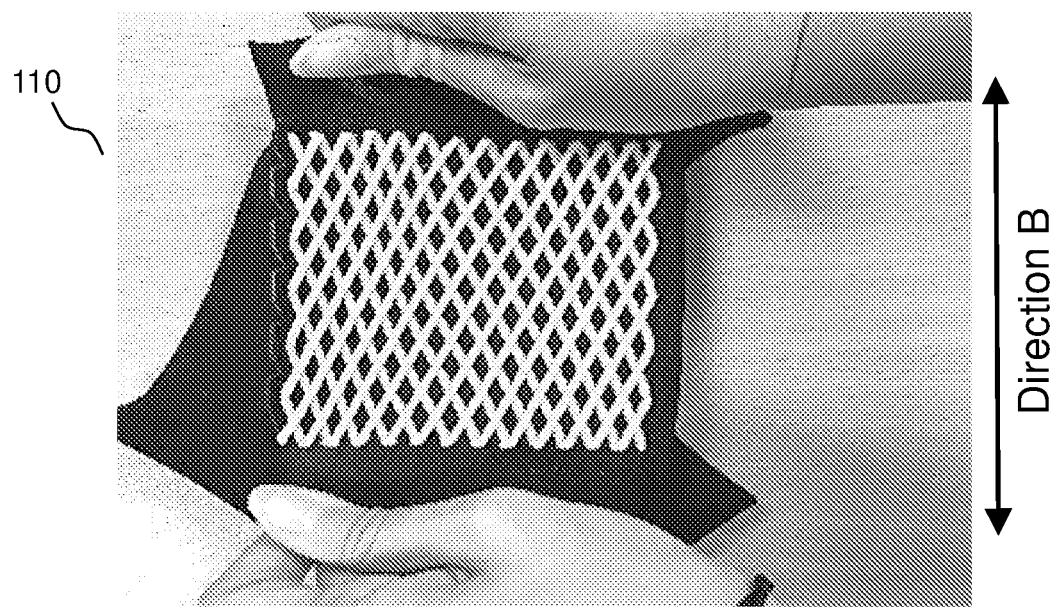

In the exemplary embodiment of the mechanical metamaterial structure 110 as shown in FIG. 1A, the diamond structures are asymmetrical and thus, provides anisotropic material properties. FIG. 3A and FIG. 3B show the mechanical metamaterial structure 110 of FIG. 1A being stretched in different directions according to various embodiments. For example, FIG. 3A and FIG. 3B show the mechanical metamaterial structure 110 of FIG. 1A being stretched in different orthogonal directions. Referring to FIG. 3A, in one direction (direction A as shown), applying the axial force allows the mechanical metamaterial structure 110 to stretch easily. Referring to FIG. 3B, applying the axial force in the transverse direction (direction B) allows the mechanical metamaterial structure 110 to stretch less easily. Accordingly, the mechanical metamaterial structure 110 may thus be printed to create customized tensile properties in different regions and/or directions. According to various embodiments, these properties of the mechanical metamaterial structure 110 may be influenced by parameters such as type of material, geometric shape, size of geometric shape and thickness of shape. By varying these parameters, the desired properties of the mechanical metamaterial structure 110 may be configured.

According to various embodiments, the mechanical metamaterial structure may be configured to have different elastic deformation profile in different regions and/or directions.

Figure 4:
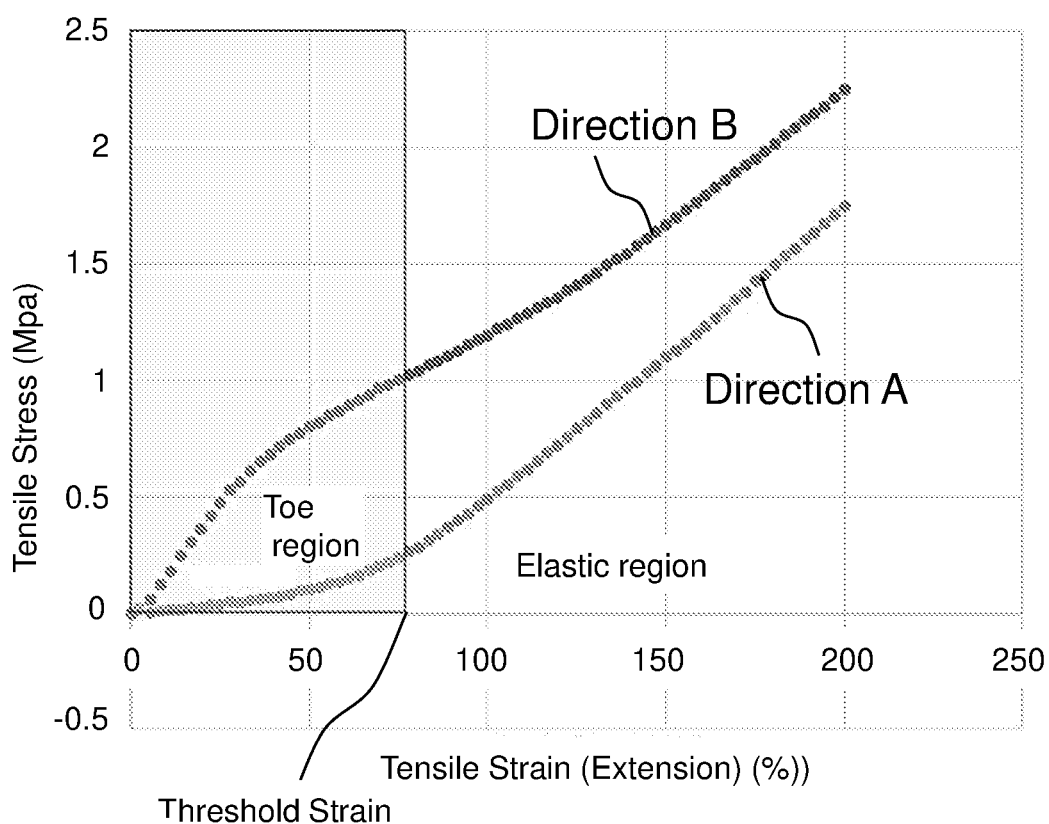
FIG. 4 shows a stress-strain diagram based on tensile stress test of the mechanical metamaterial structure of FIG. 1A in direction A of FIG. 3A and in direction B of FIG. 3B according to various embodiments.

FIG. 4 shows a stress-strain diagram based on tensile stress test of the mechanical metamaterial structure 110 of FIG. 1A in direction A of FIG. 3A and in direction B of FIG. 3B according to various embodiments. As shown, according to various embodiments, two different stress-strain curve representing two different elastic deformation profile may be obtained for the mechanical metamaterial structure 110 of FIG. 1A. According to various embodiments, for direction A, the mechanical metamaterial structure 110 of FIG. 1A may have a stress-strain curve resembling a viscoelastic behavior of a skeletal soft tissue, such as a ligament. Accordingly, the mechanical metamaterial structure 110 of FIG. 1A may be considered to be biomimetic in this regard. As shown in FIG. 4, the stress-strain curve of the mechanical metamaterial structure 110 of FIG. 1A in direction A may have a two-stage elastic deformation profile with an initial toe region (or a first stage) having an increasing elastic modulus and, subsequently, a substantially linear elastic region (or a second stage). According to various embodiments, the toe region (or the first stage) may have a stress-strain curve that is concave upwards and the linear elastic region (or the second stage) may have a stress-strain curve that is straight. According to various embodiments, the toe region (or the first stage) may crossover to the linear elastic region (or the second stage) at a predetermined strain threshold of the mechanical metamaterial structure 110. According to various embodiments, wherein the toe region (or the first stage) of the elastic deformation profile may be of a higher compliance (or lower stiffness) than the linear elastic region (or the second stage) of the elastic deformation profile.

According to various embodiments, two or more mechanical metamaterial structures may be combined in "series" or in "parallel" to create a 'hybrid' mechanical metamaterial structure. According to various embodiments, two or more mechanical metamaterial structures may be constructed in "series" or in "parallel" with similar or dissimilar materials. According to various embodiments, the mechanical properties (such as the elastic modulus) of the brace may be configured according to the needs of the user.

According to various embodiments, the brace may be customized to each individual (or user). According to various embodiments, an anthropometry data and a range of motion of the body structure (for example a joint) of the individual may be obtained. According to various embodiments, the body profile may be 3D scanned and the skin's strain profile may be obtained using methods such as through the 3D motion capture. According to various embodiments, the major regions of the brace may be identified with reference to the body structure. According to various embodiments, the major regions of the brace may include areas of unrestrictive and restrictive movement (whereby movement beyond the functional range of motion may be restricted); and anchor regions which support structures such as straps may be added to anchor or secure the brace to bony parts of the body structure. According to various embodiments, an external brace for covering over the body structure may then be generated based on each individual's requirements. According to various embodiments, each customized brace may then be printed.

Figure 5:
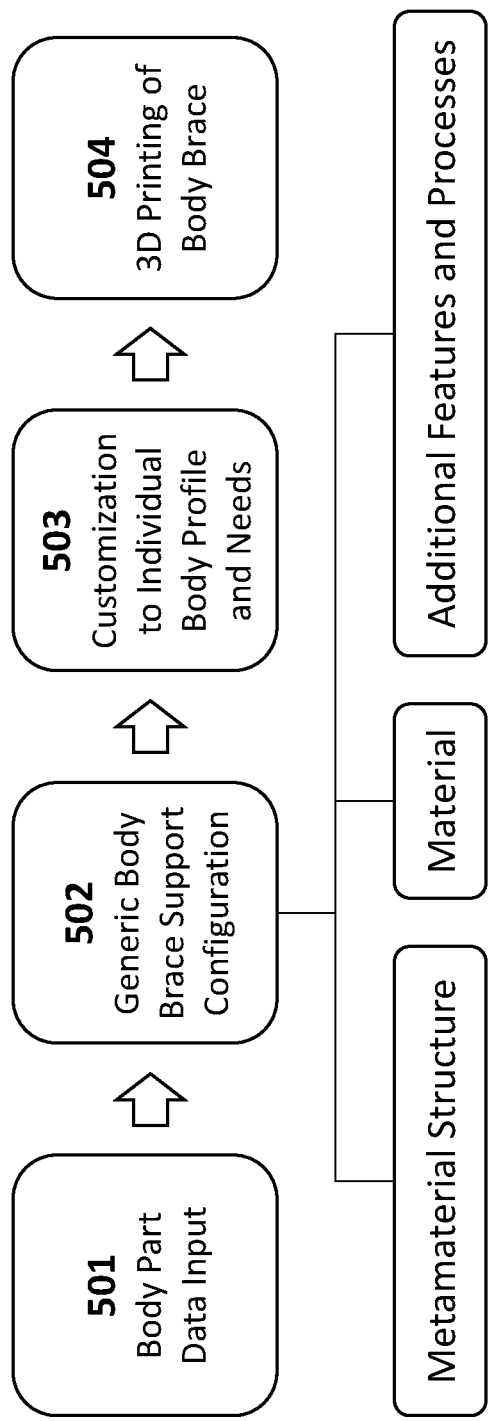
FIG. 5 shows a flow chart illustrating a fabrication process or method of a customised 'active' body brace, incorporating mechanical metamaterial structures, according to various embodiments.

FIG. 5 shows a flow chart illustrating a fabrication process or method of the customised 'active' body brace, incorporating mechanical metamaterial structures, according to various embodiments. According to various embodiments, in 501, relevant body part data may be obtained. The type of data may depend on the applications of the body brace. According to various embodiments, the body part data may be obtained using various methods, such as through physical measurements, data collection through a mobile phone application, motion capture or through 3D scanning (not necessarily 3D data all the time). According to various embodiments, the type of data depends on the applications of the body brace. According to various embodiments, in 502, a generic body brace support may be configured by selecting the type of mechanical metamaterial structure, the material to be used, and structural arrangement and features of the brace. According to various embodiments, the step in 502 may form the essential part of the process where the generic body brace configuration may be established. According to various embodiments, in 503, brace customisation for each individual body profile and needs may be carried out. According to various embodiments, in 504, the product may finally be 3D printed.

According to various embodiments, in 502, once the mechanical metamaterial structure has been selected, configuration of a generic body brace may be carried out. According to various embodiments, configuring the generic body brace may include identifying the body brace application and the body joint motion. According to various embodiments, functional range of body joint motion may be determined by motion measurement or motion analysis of the body joint. According to various embodiments, motion analysis may be carried out through kinematics motion analysis. According to various embodiments, motion measurement may include physical motion measurement by goniometers or dynamometers or from other machines. According to various embodiments, configuring the generic body brace may further include selecting regions of unrestrictive and restrictive movement (beyond functional range of motion). According to various embodiments, for each application, regions to attach different configurations of the mechanical metamaterial structure, customization and anchor regions may have to be identified. According to various embodiments, additional features and support structures such as straps may be added to anchor or secure the body brace to bony structures of the body. According to various embodiment, once the generic configuration of the brace has been established in 502, the customizable parameters may then be adjusted to meet each individual's body profile and needs in 503.

Figure 6:
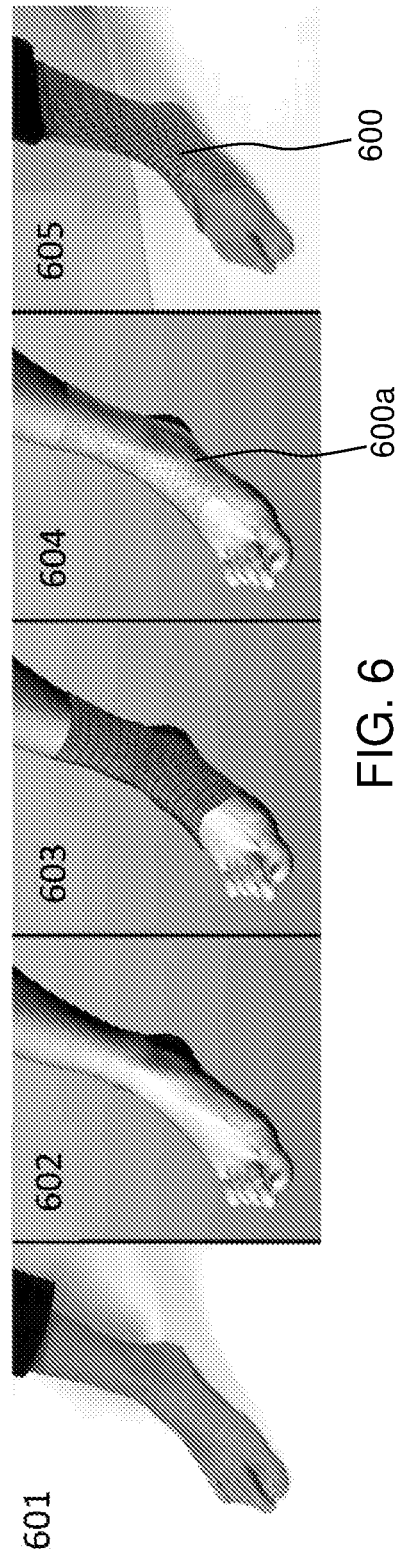
FIG. 6 shows an illustration of a fabrication sequence of an ankle brace according to various embodiments.

FIG. 6 shows an illustration of a fabrication sequence 601 to 605 of an ankle brace 600 according to various embodiments. Sequence 601 shows a foot and an ankle joint of a user which requires the brace 600. Sequence 602 shows a 3D scan of the foot and the ankle joint in CAD drawing. According to various embodiments, the 3D scan may be obtained through the 3D scanning of the foot using a handheld 3D scanner. Sequence 603 shows the contour retopology mapping of the foot and the ankle in CAD (shaded region). According to various embodiments, the contour retopology mapping may recreate a corresponding surface model that may be optimal for post-processing. According to various embodiments, if required, the surface model may then be split into a 2D surface for configuration. According to various embodiments, the mechanical metamaterial structure may be configured differently at different regions, thus creating customized mechanical properties based on the application. Sequence 604 shows the ankle brace model 600a with the configured mechanical metamaterial structure overlay on the contour map in CAD (shaded region). Sequence 605 shows the brace 600 in the unrolled form, 3D printed and fitted on the foot.

Figures 7A, 7B:
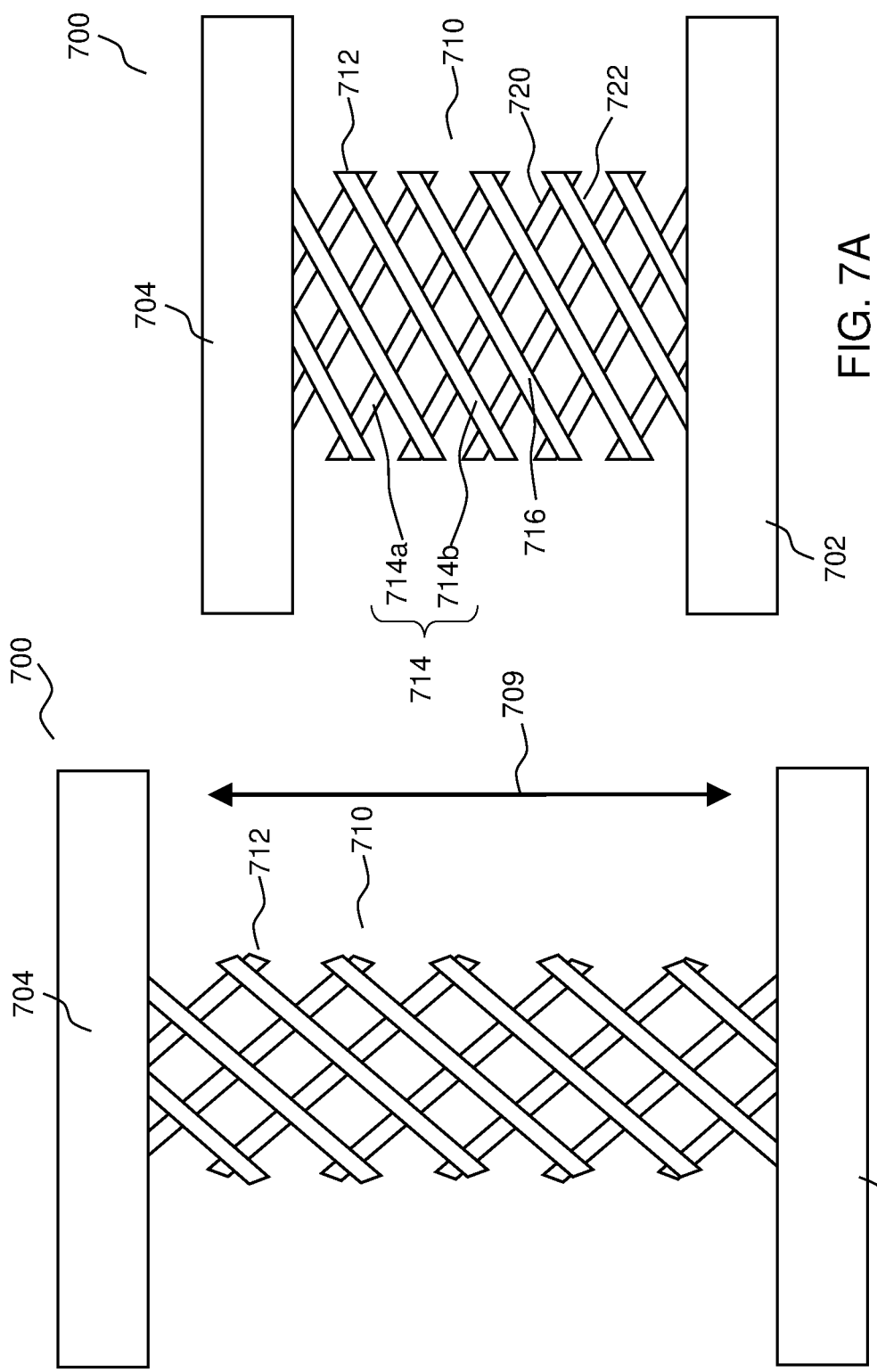
FIG. 7A to FIG. 7C show schematic diagrams of a brace according to various embodiments.
Figure 7C:
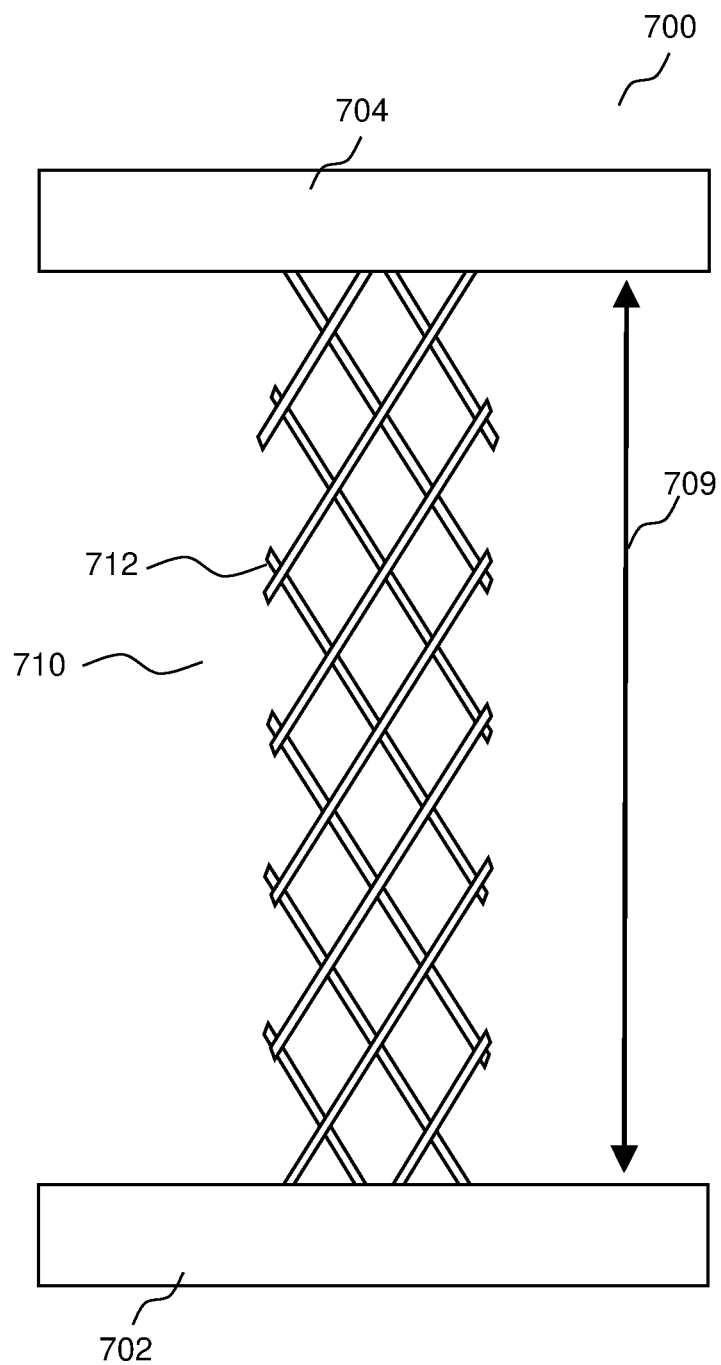

FIG. 7A to FIG. 7C show schematic diagrams of a brace 700 according to various embodiments. FIG. 7A shows the brace 700 in an unstretched or untensioned state according to various embodiments. According to various embodiments, the brace 700 may be configured for a body joint (not shown) between at least two portions of a body (e.g. a first body portion and a second body portion). According to various embodiments, the brace may include at least two anchor regions 702, 704. According to various embodiments, the brace 700 may include a first 702 of the at least two anchor regions (or a first anchor region) configured to hold the brace 700 to a first of the at least two portions of the body (or the first body portion). According to various embodiments, the brace 700 may include a second 704 of the at least two anchor regions (or a second anchor region) configured to hold the brace 700 to a second of the at least two portions of the body (or the second body portion). According to various embodiments, the at least two anchor regions 702, 704 (or first anchor region 702 and the second anchor region 704) may include, but not limited to, Velcro straps, elastic bands, belt and buckle, and/or strings which may allow a user to anchor or secure the respective anchor regions 702, 704 to respective portions of the body for wearing the brace 700 over the body joint in a manner such that the brace 700 is supporting and/or protecting the body joint. According to various embodiments, the brace 700 may include two or more anchor regions 702, 704.

According to various embodiments, the brace 700 may include a mechanical metamaterial region 710 between the at least two anchor regions 702, 704 (or the first anchor region 702 and the second anchor region 704). Accordingly, the mechanical metamaterial region 710 may be located in an intermediate section of the brace 700, and may be connecting the at least two anchor regions 702, 704. Hence, the mechanical metamaterial region 710 may spread across the body joint between the at least two portions of the body when the brace is being worn. According to various embodiments, the mechanical metamaterial region 710 may be configured to define its mechanical properties by its structure. Accordingly, depending on the function of the brace, the desired mechanical properties may be achieved by configuring the structure of the mechanical metamaterial region 710.

According to various embodiments, the mechanical metamaterial region 710 may include a mesh structure 712 having a plurality of links 714 and nodes 716 forming repeating shapes. According to various embodiments, as shown, the repeating shapes may include repeating polygon shapes, wherein the plurality of links 714 may be straight links. According to various embodiments, not shown, the repeating shapes may include repeating curvilinear shapes, wherein the plurality of links may be curved links. According to various embodiments, the mesh structure 712 may be a network or an arrangement of links 714 connected at respective nodes in a manner such that each unit cell of the mesh structure 712, which is defined by a series of links 714 forming a closed loop, is of a closed shape. According to various embodiments, the series of links 714 forming respective unit cell of the mesh structure 712 may enclose or surround a space. According to various embodiments, when the repeating shapes are repeating polygon shapes, the polygon shape may include, but not limited to, diamond, triangle, rhombus, parallelogram, kite, pentagon, hexagon, honeycomb, or octagon. According to various embodiments, each of the plurality of links 714 may include, but not limited to, a strut, a rod, or a post. According to various embodiments, when the repeating shapes are repeating curvilinear shapes, the curvilinear shape may include, but not limited to, ellipse, oval or circle. According to various embodiments, each of the plurality of links may include, but not limited to, a curve strut, a curve rod, or a curve post. According to various embodiments, the mechanical metamaterial region 710 may be formed by additive manufacturing. According to various embodiments, additive manufacturing may include 3D printing. According to various embodiments, 3D printing may include 3D printing of elastic polymer.

According to various embodiments, each node 716 may fixedly connect two or more links 714. According to various embodiments, the two or more links 714 may be integrally joined at respective node 716. According to various embodiments, each node 716 may be a point which the two or more links 714 meet or intersect in a manner such that they are fixed with respect to each other at the point. According to various embodiments, each link 714 may be configured to be capable of flexing elastically about respective node 716. According to various embodiments, each link 714 may be bendable or capable of bowing at respective end portion in the vicinity of the respective node 716. According to various embodiments, each link 714 may be configured to be capable of deforming elastically in respective axial direction. According to various embodiments, each link 714 may be extended or lengthen axially via deforming the material of the respective link 714 to change its shape and dimensions.

According to various embodiments, the mesh structure 712 may be configured to have a two-stage elastic deformation profile along a main tension direction 709. For example, the two-stage elastic deformation profile may be similar to the stress-strain curve as shown in FIG. 2 or the stress-strain curve of direction A as shown in FIG. 4. According to various embodiments, the main tension direction 709 may be oriented to extend between the at least two anchor regions 702, 704. Accordingly, when the at least two anchor regions 702, 704 are being pulled apart from each other, a tensile force may be acting on the mesh structure 712 along the main tension direction 709. According to various embodiments, the two-stage elastic deformation profile may include a first stage which is characterized by high deformation and low force (or high compliance or low stiffness), and a second stage which is characterized by low deformation and high force (or low compliance or high stiffness). Accordingly, in the first stage, the mesh structure 712 may be extended or stretched easily with a low amount of tensile force. However, in the second stage, the mesh structure 712 may only be extended or stretched by a significant increase in the amount of tensile force. According to various embodiments, the first stage may crossover to the second stage at a predetermined strain threshold of the mesh structure 712. According to various embodiments, the first stage of the elastic deformation profile may have a higher compliance (or lower stiffness) over the second stage of the elastic deformation profile. FIG. 7B shows the brace being tensioned in the first stage of deformation according to various embodiments. FIG. 7C shows the brace being tensioned in the second stage of deformation according to various embodiments.

According to various embodiments, in the first stage, the plurality of links 714 may be elastically flex about corresponding nodes 716 in a manner which transversely compresses the repeating shapes (or the repeating polygon shapes as shown in FIG. 7A to 7C) with respect to the main tension direction 709 and lengthen the repeating shapes in the main tension direction 709 so as to provide the first stage of elastic deformation of the mesh structure 712 in the main tension direction 709. According to various embodiments, in the first stage, the plurality of links 714 may be flexed towards the main tension direction 709 such that adjacent links 714 connected at respective nodes 716 may be flexed and pressed toward each other. Accordingly, each unit cell of the shape may reduce in a transverse width (which is perpendicular to the main tension direction 709) and may increase in length along the main tension direction 709.

According to various embodiments, in the second stage, the plurality of links 714 may be elastically deformed axially in a manner which stretches the repeating shapes in the main tension direction 709 so as to provide the second stage of elastic deformation of the mesh structure 712 in the main tension direction 709. According to various embodiments, in the second stage, the plurality of links 714 may have reached respective maximum flex or bow. Therefore, to further extend or stretch the mesh structure 712, respective link 714 may be deformed elastically in respective axial direction. According to various embodiments, a significantly higher tensioning force may be required in the second stage, in comparison to the tensioning force in the first stage, to elastically deform the respective link 714 in the respective axial direction so as to change the shape and dimension of the respective link 714 in order to extend or lengthen the respective link 714 in the respective axial direction. The extension or lengthening of the respective link 714 may in turn result in the further extension of the mesh structure 712.

According to various embodiments, the mesh structure 712 may be a multi-layered structure with links 714 oriented in a same direction formed in a same layer. According to various embodiments, when the mesh structure 712 includes links 714 and nodes 716 forming a uniform repeating diamond shape pattern as shown in FIG. 7A to FIG. 7C, the mesh structure 712 may include two layers 720, 722. The first layer 720 may include a first set of parallel diagonal strips which is a first set of links 714a oriented in the same first direction. The second layer 722 may include a second set of parallel diagonal strips angled off the first set of parallel diagonal strips and which may be a second set of links 714b oriented in the same second direction. The second direction being at an angle with respect to the first direction.

According to various embodiments, the shapes (or the polygon shapes as shown in FIG. 7A to FIG. 7C) of the mesh structure 712 may include asymmetrical shapes (or asymmetrical polygon shapes). According to various embodiments, by having asymmetrical shapes, the mesh structure 712 may exhibit anisotropic mechanical properties. According to various embodiments, the mesh structure 712 may include the two-stage elastic deformation profile along the main tension direction 709 and may include a different elastic deformation profile along a transverse direction which is orthogonal to the main tension direction 709.

According to various embodiments, the brace 700 may include a fabric (not shown) forming a base of the mechanical metamaterial region 710 on which the mesh structure 712 of the mechanical metamaterial region 710 is attached. Accordingly, the fabric may serve as a substrate on which the mesh structure 712 of the mechanical metamaterial region 710 may be formed or printed. According to various embodiments, the fabric may be an elastic fabric. According to various embodiments, the fabric may be through out the brace 700. Accordingly, the fabric may form a base of at least a part of or the entire brace 700.

Figure 8:
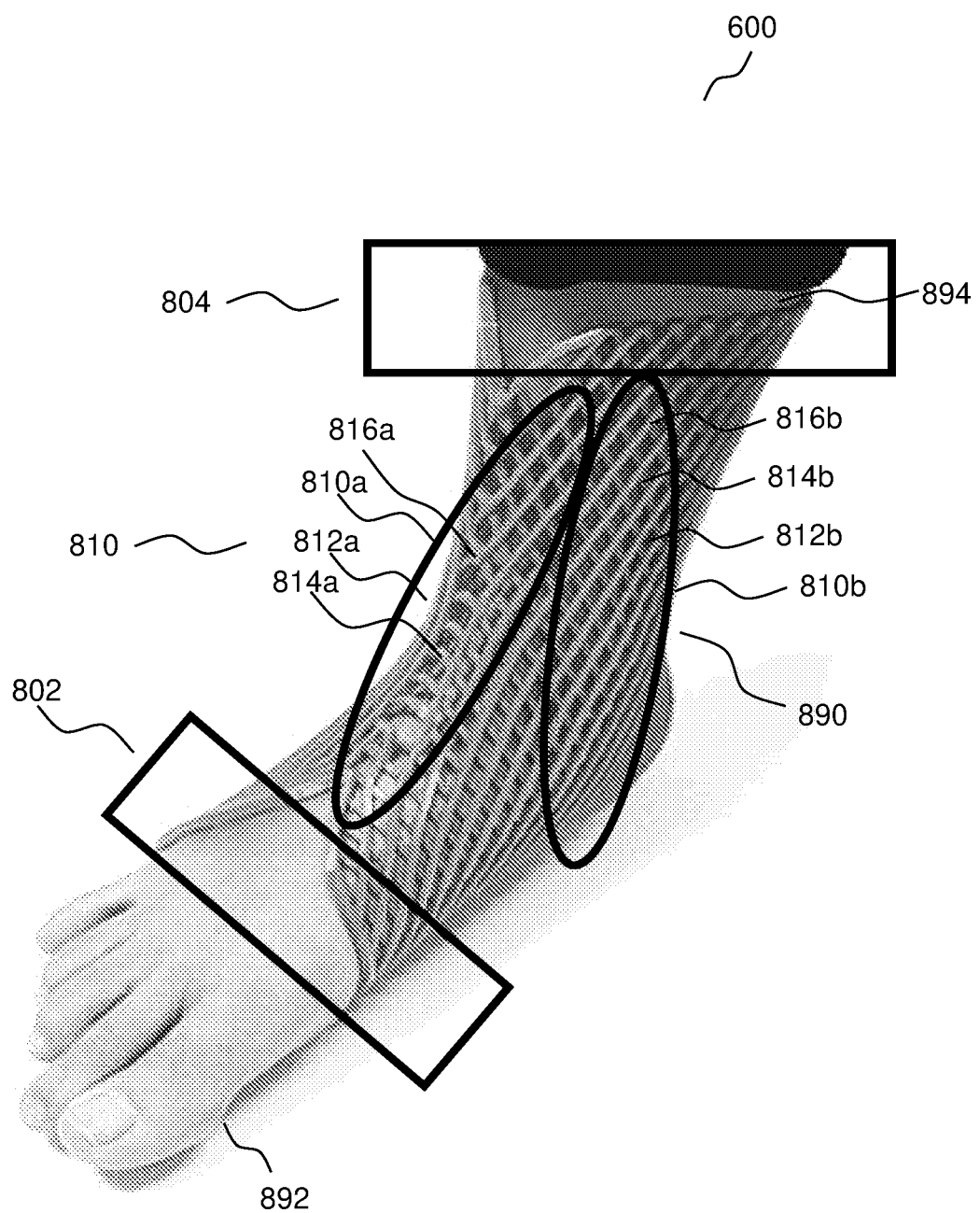
FIG. 8 shows an enlarged view of the ankle brace of FIG. 6 according to various embodiments.

FIG. 8 shows an enlarged view of the ankle brace 600 of FIG. 6 according to various embodiments. As shown, the ankle brace 600 may include a mechanical metamaterial region 810 with geometric patterns of diamond shapes, which are similar to that of the mechanical metamaterial structure 110 as shown in FIG. 1A. According to various embodiments, the ankle brace 600 may include at least two anchor regions 802, 804 (or a first anchor region 802 and a second anchor region 804) which straps may be applied to hold the ankle brace 600 to the bony structures of the body portions. According to various embodiments, the mechanical metamaterial region 810 of the ankle brace 600 may include a first portion 810a which the functional range of motion of the ankle joint may be required and which the ankle joint may need to be restricted beyond the functional range of motion so as to minimise injury risk. According to various embodiments, the diamond shapes of the first portion 810a of the mechanical metamaterial region 810 may be configured and oriented with the direction A as shown in FIG. 3A aligned to the direction of the range of motion of the ankle joint such that the first portion 810a of the mechanical metamaterial region 810 may have the two-stage elastic deformation profile along said direction. According to various embodiments, the mechanical metamaterial region 810 of the ankle brace 600 may include a second portion 810b which may need to restrict movement of the ankle joint. According to various embodiments, the diamond shapes of the second portion 810b of the mechanical metamaterial region 810 may be oriented with the direction B as shown in FIG. 3B aligned to the direction which needs to have restricted movement.

According to various embodiments, the brace 600 may be configured for a body joint (such as the ankle joint 890 as shown in FIG. 8) between at least two portions of a body, or a first body portion (i.e. the foot 892) and a second body portion (i.e. the lower leg 894). According to various embodiments, the brace 600 may include a first 802 of the at least two anchor regions (or the first anchor region 802) configured to hold the brace 600 to a first of the at least two portions of the body. According to various embodiments, the brace 600 may include a second 804 of the at least two anchor regions (or the second anchor region 804) configured to hold the brace 600 to a second of the at least two portions of the body. According to various embodiments, the at least two anchor regions 802, 804 (or the first anchor region 802 and the second anchor region 804) may be configured to be anchored or secured to the respective first and second of the at least two portions of the body with, but not limited to, Velcro straps, elastic bands, belt and buckle, and/or strings for wearing the brace 600 over the body joint in a manner such that the brace 600 is supporting and/or protecting the body joint. According to various embodiments, the brace 600 may include two or more anchor regions 802, 804.

According to various embodiments, the brace 600 may include the mechanical metamaterial region 810 between the at least two anchor regions 802, 804 (or the first anchor region 802 and the second anchor region 804). Accordingly, the mechanical metamaterial region 810 may be located in an intermediate section of the brace 600, and may be connecting the at least two anchor regions 802, 804 (or the first anchor region 802 to the second anchor region 804). Hence, the mechanical metamaterial region 810 may spread across the body joint between at least two portions of the body (or the first body portion and the second body portion) when the brace is being worn. According to various embodiments, the mechanical metamaterial region 810 may be configured to provide the desired mechanical properties for supporting and/or protecting the body joint. According to various embodiments, the mechanical metamaterial region 810 may be formed by additive manufacturing. According to various embodiments, additive manufacturing may include 3D printing. According to various embodiments, 3D printing may include 3D printing of clastic polymer.

According to various embodiments, the first portion 810a of the mechanical metamaterial region 810 may include a mesh structure 812a having a plurality of links 814a and nodes 816a forming repeating shapes. According to various embodiments, as shown, the repeating shapes may include repeating polygon shapes, wherein each of the plurality of links 814a may be a straight link. According to various embodiments, not shown, the repeating shapes may include repeating curvilinear shapes, wherein each of the plurality of link may be a curved link. According to various embodiments, the mesh structure 812a may be a network or an arrangement of links 814a connected at respective nodes in a manner such that each unit cell of the mesh structure 812a, which is defined by a series of links 814a forming a closed loop, is of a closed shape. According to various embodiments, the series of links 814a forming respective unit cell of the mesh structure 812a may enclose or surround a space. According to various embodiments, when the repeating shapes are repeating polygon shapes, the polygon shape may include, but not limited to, diamond, triangle, rhombus, parallelogram, kite, pentagon, hexagon, honeycomb, or octagon. According to various embodiments, each of the plurality of links 814a may include, but not limited to, a strut, a rod, or a post. According to various embodiments, when the repeating shapes are repeating curvilinear shapes, the curvilinear shape may include, but not limited to, ellipse, oval or circle. According to various embodiments, each of the plurality of links may include, but not limited to, a curve strut, a curve rod, or a curve post.

According to various embodiments, each node 816a may fixedly connect two or more links 814a. According to various embodiments, the two or more links 814a may be integrally joined at respective node 816a. According to various embodiments, each node 816a may be a point which the two or more links 814a meet or intersect in a manner such that they are fixed with respect to each other at the point. According to various embodiments, each link 814a may be configured to be capable of flexing elastically about respective node 816a. According to various embodiments, each link 814a may be bendable or capable of bowing at respective end portion towards the respective node 816a. According to various embodiments, each link 814a may be configured to be capable of deforming elastically in respective axial direction. According to various embodiments, each link 814a may be extended or lengthen axially via deforming the material of the respective link 814a to change its shape and dimensions.

According to various embodiments, the mesh structure 812a of the first portion 810a of the mechanical metamaterial region 810 may be configured to have a two-stage clastic deformation profile along a main tension direction. According to various embodiments, the main tension direction may be oriented to extend between the at least two anchor regions 802, 804 (or the first anchor region 802 and the second anchor region 804), which may coincide with the direction of functional range of motion of the joint. Accordingly, when the at least two anchor regions 802, 804 (or the first anchor region 802 and the second anchor region 804) are being pulled apart from each other, a tensile force may be acting on the mesh structure 812a along the main tension direction. According to various embodiments, the two-stage elastic deformation profile may include a first stage which is characterized by high deformation and low force (or high compliance or low stiffness), and a second stage which is characterized by low deformation and high force (or low compliance or high stiffness). Accordingly, in the first stage, the mesh structure 812a of the first portion 810a of the mechanical metamaterial region 810 may be extended or stretched easily with a low amount of tensile force. However, in the second stage, the mesh structure 812a of the first portion 810a of the mechanical metamaterial region 810 may only be extended or stretched by a significant increase in the amount of tensile force. According to various embodiments, the first stage may crossover to the second stage at a predetermined strain threshold of the mesh structure 812a. According to various embodiments, the first stage of the elastic deformation profile may have a higher compliance (or lower stiffness) over the second stage of the elastic deformation profile.

According to various embodiments, in the first stage, the plurality of links 814a may be elastically flex about corresponding nodes 816a in a manner which transversely compresses the repeating shapes (or the repeating polygon shapes as shown in FIG. 8) with respect to the main tension direction and lengthen the repeating shapes in the main tension direction so as to provide the first stage of elastic deformation of the mesh structure 812a of the first portion 810a of the mechanical metamaterial region 810 in the main tension direction. According to various embodiments, in the first stage, the plurality of links 814a may be flexed towards the main tension direction such that corresponding adjacent links 814a connected at respective nodes 816a may be flexed and pressed toward each other. Accordingly, each unit cell of the shape may reduce in a transverse width (which is perpendicular to the main tension direction) and may increase in length along the main tension direction.

According to various embodiments, in the second stage, the plurality of links 814a may be elastically deformed axially in a manner which stretches the repeating shapes in the main tension direction so as to provide the second stage of elastic deformation of the mesh structure 812a of the first portion 810a of the mechanical metamaterial region 810 in the main tension direction. According to various embodiments, in the second stage, the plurality of links 814a has reached respective maximum flex or bow. Therefore, to further extend or stretch the mesh structure 812a of the first portion 810a of the mechanical metamaterial region 810, respective link 814a may be deformed elastically in respective axial direction. According to various embodiments, a significantly higher tensioning force may be required in the second stage, in comparison to the tensioning force in the first stage, to elastically deform the respective link 814a in the respective axial direction so as to change the shape and dimension of the respective link 814a in order to extend or lengthen the respective link in the respective axial direction. The extension or lengthening of the respective link 814a may in turn result in the further extension of the mesh structure 812a.

According to various embodiments, the mesh structure 812a of the first portion 810a of the mechanical metamaterial region 810 may be a multi-layered structure with links 814a oriented in a same direction formed in a same layer. Accordingly, each layer may include links 814a that are oriented in the same direction.

According to various embodiments, the shapes (or the polygon shapes as shown in FIG. 8) of the mesh structure 812a of the first portion 810a of the mechanical metamaterial region 810 may include asymmetrical shapes (or asymmetrical polygon shapes). According to various embodiments, by having asymmetrical shapes, the mesh structure 812a may exhibit anisotropic mechanical properties. According to various embodiments, the mesh structure 812a may include the two-stage elastic deformation profile along the main tension direction and may include a different elastic deformation profile along a transverse direction which is orthogonal to the main tension direction.

According to various embodiments, the brace 600 may include a fabric (not shown) forming a base of the mechanical metamaterial region 810 on which the mesh structure 812a of the first portion 810a of the mechanical metamaterial region 810 may be attached. Accordingly, the fabric may serve as a substrate on which the mesh structure 812a of the first portion 810a of the mechanical metamaterial region 810 may be formed or printed. According to various embodiments, the fabric may be an elastic fabric. According to various embodiments, the fabric may be through out the brace 600. Accordingly, the fabric may form a base of at least a part of or the entire brace 600.

According to various embodiments, the second portion 810b of the mechanical metamaterial region 810 of the brace 600 may include a secondary mesh structure 812b arranged in parallel with respect to the mesh structure 812a of the first portion 810a of the mechanical metamaterial region 810. According to various embodiments, the first portion 810a and the second portion 810b of the mechanical metamaterial region 810 of the brace 600 may be arranged side-by-side such that each is extending between the at least two anchor regions 802, 804 (or the first anchor region 802 and the second anchor region 804). According to various embodiments, the secondary mesh structure 812b may include a plurality of secondary links 814b and secondary nodes 816b forming repeating secondary shapes. According to various embodiments, as shown, the repeating secondary shapes may include repeating secondary polygon shapes, wherein each of the plurality of secondary links 814b may be a straight link. According to various embodiments, not shown, the repeating shapes may include repeating curvilinear shapes, wherein each of the plurality of links may be a curved link. According to various embodiments, the secondary mesh structure 812b may be a network or an arrangement of secondary links 814b connected at respective secondary nodes 816b in a manner such that each unit cell of the secondary mesh structure 812b, which is defined by a series of secondary links 814b forming a closed loop, is of a closed shape. According to various embodiments, the series of secondary links 814b forming respective unit cell of the secondary mesh structure 812b may enclose or surround a space. According to various embodiments, when the repeating secondary shapes are repeating secondary polygon shapes, the secondary polygon shape may include, but not limited to, diamond, triangle, rhombus, parallelogram, kite, pentagon, hexagon, honeycomb, or octagon. According to various embodiments, each of the plurality of secondary links 814b may include, but not limited to, a strut, a rod, or a post. According to various embodiments, when the repeating secondary shapes are repeating secondary curvilinear shapes, the secondary curvilinear shape may include, but not limited to, ellipse, oval or circle. According to various embodiments, each of the plurality of secondary links may include, but not limited to, a curve strut, a curve rod, or a curve post. According to various embodiments, each secondary node 816a may fixedly connect two or more secondary links 814a. According to various embodiments, the two or more secondary links 814a may be integrally joined at respective secondary node 816a.

According to various embodiments, the secondary shapes (or the secondary polygon shapes as shown in FIG. 8) of the secondary mesh structure 812b of the second portion 810b may be different from the shapes (or the polygon shapes as shown in FIG. 8) of the mesh structure 812a of the first portion 810a. According to various embodiments, the secondary shapes of the secondary mesh structure 812b may differ from the shapes of the mesh structure 812a in terms of any one or a combination of orientation, shapes, dimensions or link's thickness.

According to various embodiments, the mesh structure 812a and the secondary mesh structure 812b may be constructed in "parallel" with similar or dissimilar materials.

According to various embodiments, the secondary mesh structure 812b of the second portion 810b of the mechanical metamaterial region 810 may be a multi-layered structure with secondary links 814b oriented in a same direction formed in a same layer. Accordingly, each layer may include secondary links 814*b* that are oriented in the same direction.

According to various embodiments, the secondary shapes (or the secondary polygon shapes as shown in FIG. 8) of the secondary mesh structure 812*b* of the second portion 810*b* of the mechanical metamaterial region 810 may include asymmetrical shapes (or asymmetrical polygon shapes). According to various embodiments, by having asymmetrical shapes, the secondary mesh structure 812*b* may exhibit anisotropic mechanical properties.

Figure 9A:
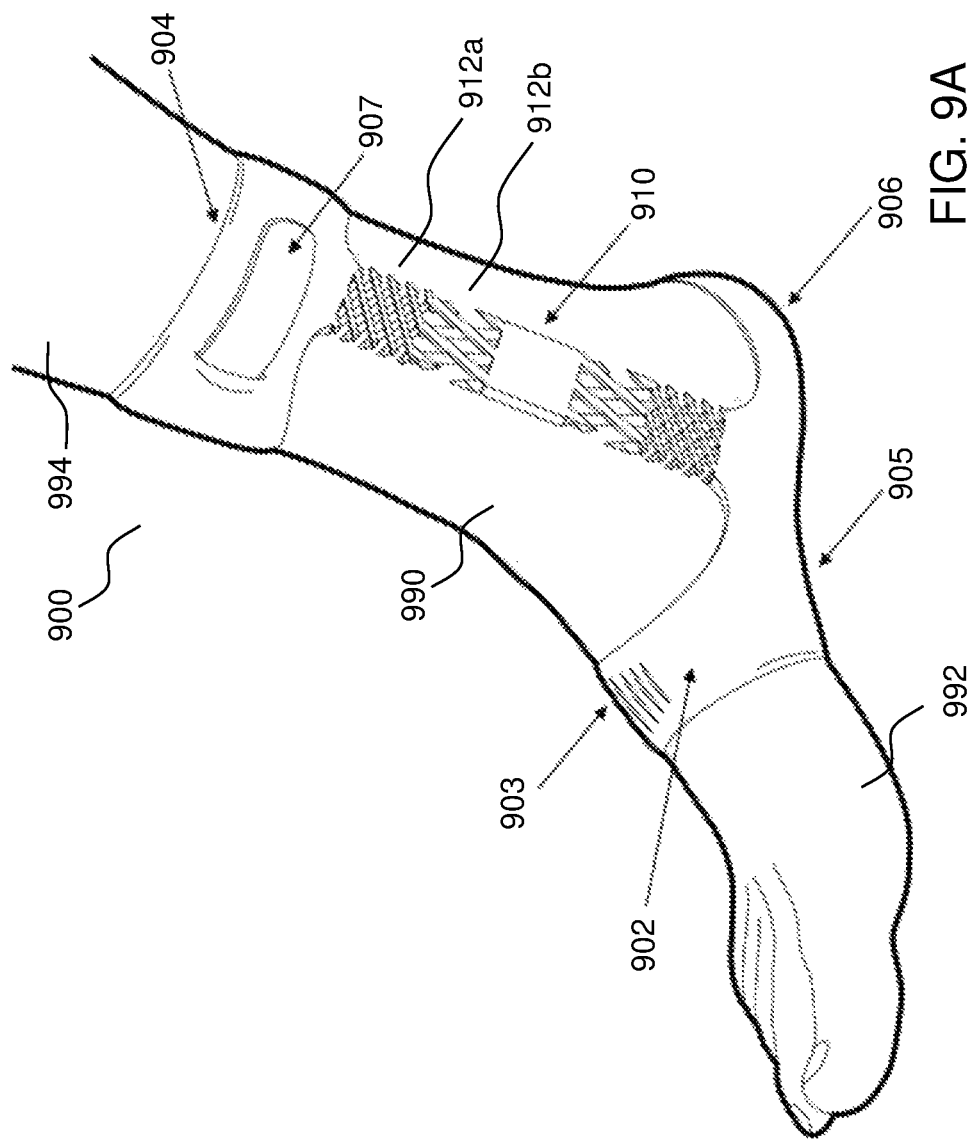
FIG. 9A shows another ankle brace for an ankle between a foot and a lower leg according to various embodiments.

FIG. 9A shows another ankle brace 900 for an ankle 990 between a foot 992 and a lower leg 994 according to various embodiments. As shown, the brace 900 may include a mechanical metamaterial region 910 using diamond mesh metamaterial structures to reduce or prevent ankle sprain injury risks. According to various embodiments, the brace 900 may include at least two anchor regions 902, 904 (or a first anchor region 902 and a second anchor region 904), which are selected anchor positions in the brace 900. According to various embodiments, a top part of the foot may be free to move and the brace 900 may not cover the top part of the foot. According to various embodiments, the mechanical metamaterial region 910 may only be along the side of the foot extending across the side of the ankle to the side of the lower leg for reducing ankle sprain injury risks. According to various embodiments, the mechanical metamaterial region 910 may be configurable and customizable to individual's needs and foot profile. According to various embodiments, the mechanical metamaterial region 910 may include a 'hybrid' metamaterial structure having two or more mesh structures 912*a*, 912*b* with different geometrically oriented unit cell. For example, as shown in FIG. 9, the 'hybrid' metamaterial structure may include different orientations of diamond mesh patterns, which may be 'selected' during the metamaterial configuration phase in step 502 of the fabrication process as shown in FIG. 5. According to various embodiments, with the mechanical metamaterial region 910, the foot may be free to move within the functional range of motion as the mechanical metamaterial region 910 may be configured to have a low Young's modulus, similar to Zone A in FIG. 2; and the foot may slow down as it moves beyond this range with greater resistance from the brace 900 as the mechanical metamaterial region 910 may be configured to have a higher Young's modulus, similar to Zone B in FIG. 2. According to various embodiments, the mechanical metamaterial region 910 may reduce the risks of the foot diving into an ankle sprain position suddenly.

According to various embodiments, a first 902 of the at least two anchor regions (or the first anchor region 902) of the brace 900 may be configured for securing or anchoring to the foot. According to various embodiments, the first 902 of the at least two anchor regions (or the first anchor region 902) of the brace 900 may be configured to include elastic material for closer fit and comfort to the foot. According to various embodiments, the first 902 of the at least two anchor regions (or the first anchor region 902) of the brace 900 may be configured to include ventilation holes 903 which may be in the form of gaps for ventilation and comfort. According to various embodiments, the first 902 of the at least two anchor regions (or the first anchor region 902) of the brace 900 may be configured to include an arch support 905 for supporting the arch of the sole of the foot. According to various embodiments, the arch support 905 may be customised. According to various embodiments, the first 902 of the at least two anchor regions (or the first anchor region 902) of the brace 900 may be configured to include an inner sole plate 906 for support the heel of the foot. According to various embodiments, the inner sole plate 906 may be modelled from 3D scanning for customised fit.

According to various embodiments, a second 904 of the at least two anchor regions (or the second anchor region 904) of the brace 900 may be configured for securing or anchoring to the lower leg. According to various embodiments, the second 904 of the at least two anchor regions (or the second anchor region 904) of the brace 900 may be configured to include adjustable Velcro straps 907 for securing or anchoring the second 904 of the at least two anchor regions (or the second anchor region 904) to the lower leg. According to various embodiments, the second 904 of the at least two anchor regions (or the second anchor region 904) of the brace 900 may be configured to include adjustable tab with Velcro straps for easy removal. According to various embodiments, the second 904 of the at least two anchor regions (or the second anchor region 904) of the brace 900 may be configured to include a silicon lining. According to various embodiments, the second 904 of the at least two anchor regions (or the second anchor region 904) of the brace 900 may be configured to include an inner padding with silicon lining for better grip on skin.

According to various embodiments, when configuring the generic body brace support in 502 of FIG. 5, the generic body brace support may include any combination or all of the features of the brace 900. According to various embodiments, when customizing the generic body brace support to meet each individual's body profile and needs in 503 of FIG. 5, body part data, such as a 3D scan of the foot, anthropometry data and range of motion may be input by the user. According to various embodiments, based on each individual data, the length of the different components of the metamaterial structure, the circumferences of the anchor support at the foot, the arch and the inner sole may be customized to meet each unique foot profile. According to various embodiments, the customised ankle brace may be 3D printed.

According to various embodiments, the brace 900 may be configured for a body joint (such as the ankle joint 990 as shown in FIG. 9A) between at least two portions of a body, or a first body part (i.e. the foot 992) and a second body part (i.e. the lower leg 994). According to various embodiments, the brace 900 may include the first 902 of the at least two anchor regions (or the first anchor region 902) configured to hold the brace 900 to the first of the at least two portions of the body. According to various embodiments, the brace 900 may include the second 904 of the at least two anchor regions (or the second anchor region 904) configured to hold the brace 900 to the second of the at least two portions of the body. According to various embodiments, the at least two anchor regions 902, 904 (or the first anchor region 902 and the second anchor region 904) may be configured to be anchored or secured to the respective portions of the at least two portions of the body with, but not limited to, Velcro straps, elastic bands, belt and buckle, and/or strings for wearing the brace 900 over the body joint in a manner such that the brace 900 is supporting and/or protecting the body joint. According to various embodiments, the brace 900 may include two or more anchor regions 902, 904.

Figure 9B:
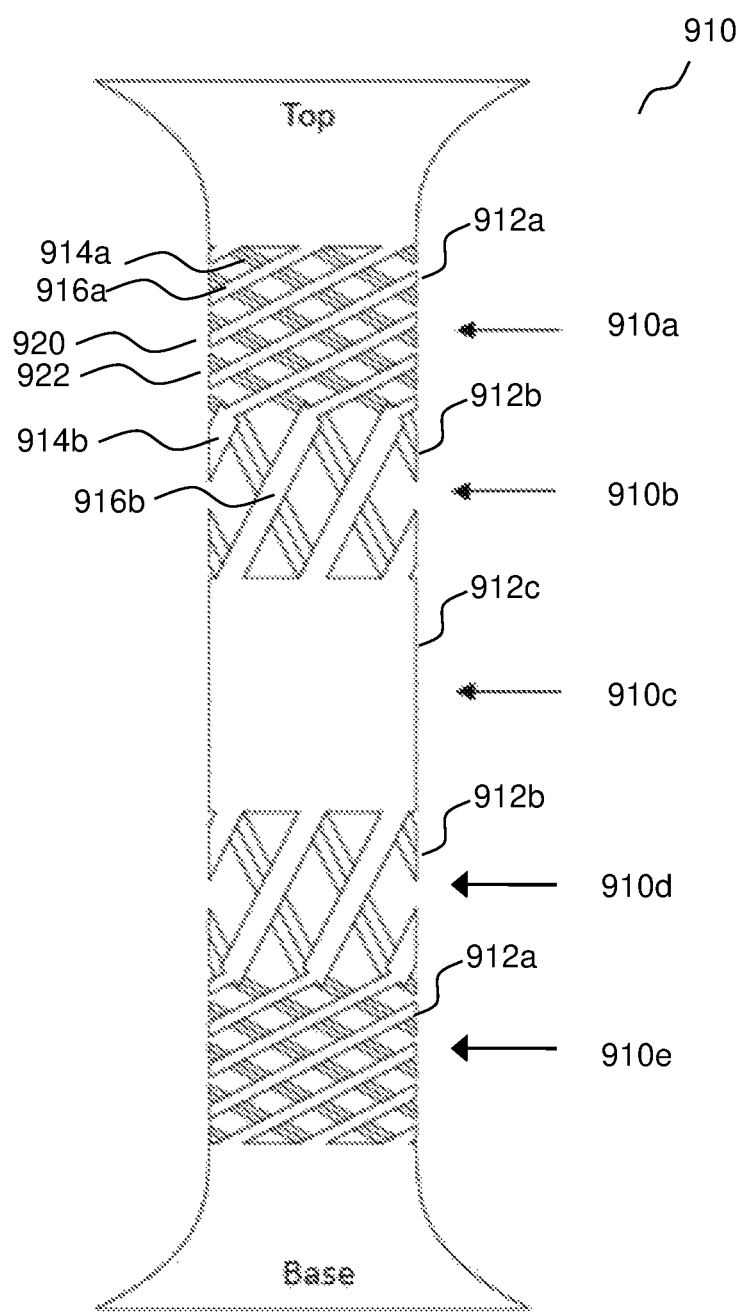
FIG. 9B shows the mechanical metamaterial region of the brace of FIG. 9A according to various embodiments.

FIG. 9B shows the mechanical metamaterial region 910 of the brace 900 according to various embodiments. According to various embodiments, the brace 900 may include the mechanical metamaterial region 910 between the at least two anchor regions 902, 904 (or the first anchor region 902 and the second anchor region 904). Accordingly, the mechanical metamaterial region 910 may be located in an intermediate section of the brace 900, and may be connecting the at least two anchor regions 902, 904 (or the first anchor region 902 to the second anchor region 904). Hence, the mechanical metamaterial region 910 may spread across the body joint (or the ankle joint 900) between the at least two portions of the body when the brace is being worn. According to various embodiments, the mechanical metamaterial region 910 may be configured to provide the desired mechanical properties for supporting and/or protecting the body joint.

According to various embodiments, the mechanical metamaterial region 910 may include two or more different portions. According to various embodiments, as shown in FIG. 9A and FIG. 9B, the mechanical metamaterial region 910 may include a first portion 910a, a second portion 910b, a third portion 910c, a fourth portion 910d and a fifth portion 910e. According to various embodiments, the third portion 910c may be between the second portion 910b and the fourth portion 910d. According to various embodiments, the first portion 910a and the fifth portion 910e may be at respective ends of the mechanical metamaterial region 910. According to various embodiments, the two or more different portions of the mechanical metamaterial region 910 may have different structure from each other. According to various embodiments, the first portion 910a may have a first mesh structure 912a. According to various embodiments, the fifth portion 910e may have the same first mesh structure 912a as the first portion 910a. According to various embodiments, the second portion 910b may have a second mesh structure 912b. According to various embodiments, the fourth portion 910d may have the same second mesh structure 912b as the second portion 910b. According to various embodiments, the first mesh structure 912a and the second mesh structure 912b may be configured to have different mechanical properties. According to various embodiments, the third portion 910c may include a single solid panel structure 912c. According to various embodiments, the mechanical properties of the single solid panel structure 912c of the third portion 910c may be defined by the materials of the single solid panel structure 912c.

According to various embodiments, the two or more different portions of the mechanical metamaterial region 910 may be arranged in series or in parallel with respect to each other. According to various embodiments, when the two or more different portions of the mechanical metamaterial region 910 are arranged in series, the two or more different portions may be arranged one after another in a direction extending between the first anchor region 902 and the second anchor region 904. According to various embodiments, when the two or more different portions of the mechanical metamaterial region 910 are arranged in parallel, the two or more different portions may be arranged side-by-side such that each portion directly extends between the first anchor region 902 and the second anchor region 904. According to various embodiments, two or more different portions of the mechanical metamaterial region 910 may be constructed in series or in parallel with similar or dissimilar materials.

According to various embodiments, the two or more different portions of the mechanical metamaterial region 910 may be integrally formed as a single unit such that the mechanical metamaterial region 910 may be a complete structural whole. According to various embodiments, the mechanical metamaterial region 910 may be formed by additive manufacturing. According to various embodiments, additive manufacturing may include 3D printing. According to various embodiments, 3D printing may include 3D printing of elastic polymer. According to various embodiments, the two or more different portions of the mechanical metamaterial region 910 may be printed integrally to form a single unitary unit or a one-piece structure.

According to various embodiments, the first mesh structure 912a of the first portion 910a of the mechanical metamaterial region 910 may include a plurality of links 914a and nodes 916a forming repeating shapes. According to various embodiments, as shown, the repeating shapes may include repeating polygon shapes, wherein each of the plurality of links 914a may be a straight link. According to various embodiments, not shown, the repeating shapes may include repeating curvilinear shapes, wherein each of the plurality of links may be a curved link. According to various embodiments, the first mesh structure 912a may be a network or an arrangement of links 914a connected at respective nodes 916a in a manner such that each unit cell of the first mesh structure 912a, which is defined by a series of links 914a forming a closed loop, is of a closed shape. According to various embodiments, the series of links 914a forming respective unit cell of the first mesh structure 912a may enclose or surround a space. As shown, according to various embodiments, the shape may be a diamond shape. According to various embodiments, when the repeating shapes are repeating polygon shapes, the polygon shape may include, but not limited to, other shapes such as triangle, rhombus, parallelogram, kite, pentagon, hexagon, honeycomb, or octagon. According to various embodiments, each of the plurality of links 914a may include, but not limited to, a strut, a rod, or a post. According to various embodiments, when the repeating shapes are repeating curvilinear shapes, the curvilinear shape may include, but not limited to, ellipse, oval or circle. According to various embodiments, each of the plurality of links may include, but not limited to, a curve strut, a curve rod, or a curve post.

According to various embodiments, each node 916a may fixedly connect two or more links 914a. According to various embodiments, the two or more links 914a may be integrally joined at respective node 916a. According to various embodiments, each node 916a may be a point which the two or more links 914a meet or intersect in a manner such that they are fixed with respect to each other at the point. According to various embodiments, each link 914a may be configured to be capable of flexing elastically about respective node 916a. According to various embodiments, each link 914a may be bendable or capable of bowing at respective end portion in the vicinity of the respective node 916a. According to various embodiments, each link 914a may be configured to be capable of deforming elastically in respective axial direction. According to various embodiments, each link 914a may be extended or lengthen axially via deforming the material of the respective link 914a to change its shape and dimensions.

According to various embodiments, the first mesh structure 912a of the first portion 910a of the mechanical metamaterial region 910 may be configured to have a two-stage elastic deformation profile along a main tension direction. According to various embodiments, the main tension direction may be oriented to extend between the at least two anchor regions 902, 904 (or the first anchor region 902 and the second anchor region 904), which may coincide with the direction of functional range of motion of the joint. Accordingly, when the at least two anchor regions (or the first anchor region 902 and the second anchor region 904) are being pulled apart from each other, a tensile force may be acting on the first mesh structure 912a along the main tension direction. According to various embodiments, the two-stage elastic deformation profile may include a first stage which is characterized by high deformation and low force (or high compliance or low stiffness), and a second stage which is characterized by low deformation and high force (or low compliance or high stiffness). Accordingly, in the first stage, the first mesh structure 912a of the first portion 810a of the mechanical metamaterial region 910 may be extended or stretched easily with a low amount of tensile force. However, in the second stage, the first mesh structure 912a of the first portion 910a of the mechanical metamaterial region 910 may only be extended or stretched by a significant increase in the amount of tensile force. According to various embodiments, the first stage may crossover to the second stage at a predetermined strain threshold of the first mesh structure 912a. According to various embodiments, the first stage of the elastic deformation profile may have a higher compliance (or lower stiffness) over the second stage elastic deformation profile.

According to various embodiments, in the first stage, the plurality of links 914a may be elastically flex about corresponding nodes 916a in a manner which transversely compresses the repeating shapes (or the repeating polygon shapes as shown in FIG. 9A and FIG. 9B) with respect to the main tension direction and lengthen the repeating shapes in the main tension direction so as to provide the first stage of elastic deformation of the first mesh structure 912a of the first portion 910a of the mechanical metamaterial region 910 in the main tension direction. According to various embodiments, in the first stage, the plurality of links 914a may be flexed towards the main tension direction such that corresponding adjacent links 914a connected at respective nodes 916a may be flexed and pressed toward each other. Accordingly, each unit cell of the shape may reduce in a transverse width (which is perpendicular to the main tension direction) and may increase in length along the main tension direction.

According to various embodiments, in the second stage, the plurality of links 914a may be elastically deformed axially in a manner which stretches the repeating shapes (or the repeating polygon shapes as shown in FIG. 9A and FIG. 9B) in the main tension direction so as to provide the second stage of elastic deformation of the first mesh structure 912a of the first portion 910a of the mechanical metamaterial region 910 in the main tension direction. According to various embodiments, in the second stage, the plurality of links 914a has reached respective maximum flex or bow. Therefore, to further extend or stretch the first mesh structure 912a of the first portion 910a of the mechanical metamaterial region 910, respective link 914a may be deformed elastically in respective axial direction. According to various embodiments, a significantly higher tensioning force may be required, in comparison to the tensioning force in the first stage, to elastically deform the respective link 914a in the respective axial direction so as to change the shape and dimension of the respective link 914a in order to extend or lengthen the respective link in the respective axial direction. The extension or lengthening of the respective link 914a may in turn result in the further extension of the first mesh structure 912a.

According to various embodiments, the first mesh structure 912a of the first portion 910a of the mechanical metamaterial region 910 may be a multi-layered structure with links 914a oriented in a same direction formed in a same layer. Accordingly, each layer may include links 914a that are oriented in the same direction. According to various embodiments, when the first mesh structure 912a includes links 914a and nodes 916a forming a uniform repeating diamond shape pattern as shown in FIG. 9A and FIG. 9B, the first mesh structure 912a may include two layers 920, 922. The first layer 920 may include a first set of parallel diagonal strips which is a first set of links 914a oriented in the same first direction. The second layer 922 may include a second set of parallel diagonal strips angled off the first set of parallel diagonal strips and which is a second set of links 914a oriented in the same second direction. The second direction being at an angle with respect to the first direction.

According to various embodiments, the shapes (or the polygon shapes as shown in FIG. 9A and FIG. 9B) of the first mesh structure 912a of the first portion 910a of the mechanical metamaterial region 910 may include asymmetrical shapes (or asymmetrical polygon shapes). According to various embodiments, by having asymmetrical shapes, the first mesh structure 912a may exhibit anisotropic mechanical properties. According to various embodiments, the first mesh structure 912a may include the two-stage elastic deformation profile along the main tension direction and may include a different elastic deformation profile along a transverse direction which is orthogonal to the main tension direction.

According to various embodiments, the brace 900 may include a fabric (not shown) forming a base of the mechanical metamaterial region 910 on which the first mesh structure 912s of the first portion 910a of the mechanical metamaterial region 910 may be attached. Accordingly, the fabric may serve as a substrate on which the first mesh structure 912a of the first portion 910a of the mechanical metamaterial region 910 may be formed or printed. According to various embodiments, the fabric may be an elastic fabric. According to various embodiments, the fabric may be through out the brace 900. Accordingly, the fabric may form a base of at least a part of or the entire brace 900.

According to various embodiments, the second portion 910b of the mechanical metamaterial region 910 of the brace 900 may include the second mesh structure 912b arranged in series with respect to the first mesh structure 912a of the first portion 910a of the mechanical metamaterial region 910. According to various embodiments, the second mesh structure 912b may include a plurality of secondary links 914b and secondary nodes 916b forming repeating secondary shapes. According to various embodiments, as shown, the repeating secondary shapes may include repeating secondary polygon shapes, wherein each of the plurality of links 914b may be a straight link. According to various embodiments, not shown, the repeating secondary shapes may include repeating secondary curvilinear shapes, wherein each of the plurality of links may be a curved link. According to various embodiments, the second mesh structure 912b may be a network or an arrangement of secondary links 914b connected at respective secondary nodes 916b in a manner such that each unit cell of the second mesh structure 912b, which is defined by a series of secondary links 914b forming a closed loop, is of a closed shape. According to various embodiments, the series of secondary links 914b forming respective unit cell of the secondary mesh structure 912b may enclose or surround a space. As shown, according to various embodiments, the secondary shape may be a diamond shape. According to various embodiments, when the repeating secondary shapes are repeating secondary polygon shapes, the secondary polygon shape may include, but not limited to, other shapes such as triangle, rhombus, parallelogram, kite, pentagon, hexagon, honeycomb, or octagon. According to various embodiments, each of the plurality of secondary links 914b may include, but not limited to, a strut, a rod, or a post. According to various embodiments, when the repeating secondary shapes are repeating secondary curvilinear shapes, the secondary curvilinear shape may include, but not limited to, ellipse, oval or circle. According to various embodiments, each of the plurality of links may include, but not limited to, a curve strut, a curve rod, or a curve post. According to various embodiments, each secondary node 916b may fixedly connect two or more secondary links 914b. According to various embodiments, the two or more secondary links 914b may be integrally joined at respective secondary node 916b. According to various embodiments, each secondary node 916b may be a point which the two or more secondary links 914b meet or intersect in a manner such that they are fixed with respect to each other at the point.

According to various embodiments, the secondary shapes (or the secondary polygon shapes as shown in FIG. 9A and FIG. 9B) of the second mesh structure 912b of the second portion 910b may be different from the shapes (or the polygon shapes as shown in FIG. 9A and FIG. 9B) of the first mesh structure 912a of the first portion 910a. According to various embodiments, the secondary shapes of the second mesh structure 912b may differ from the shapes of the first mesh structure 912a in terms of any one or a combination of orientation, shapes, dimensions or link's thickness. As shown in FIG. 9B, according to various embodiments, the secondary shapes of the second mesh structure 912b of the second portion 910b may be larger in size, thicker and in a different orientation from the shapes of the first mesh structure 912a of the first portion 910a. According to various embodiments, the first mesh structure 912a may be configured to have the two-stage elastic deformation profile along the main tension direction, while the second mesh structure 912b may have an elastic deformation profile having a high elastic modulus along the main tension direction.

According to various embodiments, the second mesh structure 912b of the second portion 910b of the mechanical metamaterial region 910 may be a multi-layered structure with the secondary links 914b oriented in a same direction formed in a same layer. Accordingly, each layer may include the secondary links 914b that are oriented in the same direction.

According to various embodiments, the secondary shapes (or the secondary polygon shapes as shown in FIG. 9A and FIG. 9B) of the second mesh structure 912b of the second portion 910b of the mechanical metamaterial region 910 may include asymmetrical shapes (or asymmetrical polygon shapes). According to various embodiments, by having asymmetrical shapes, the second mesh structure 912b may exhibit anisotropic mechanical properties.

Figure 10:
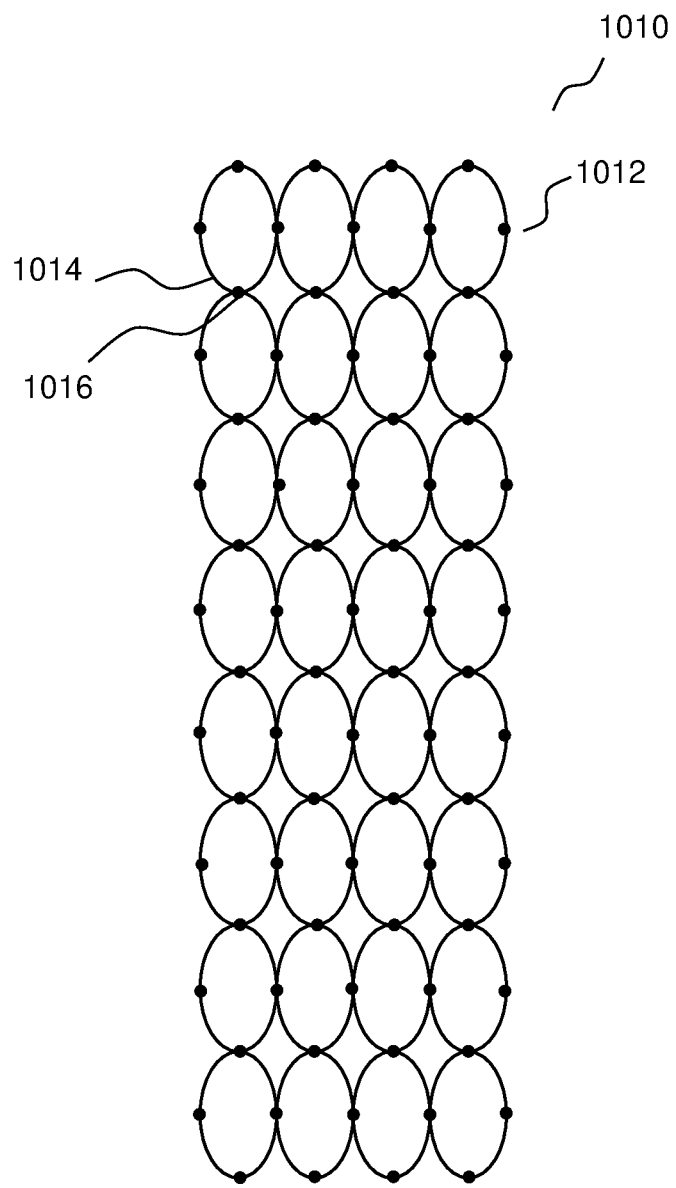
FIG. 10 shows a schematic diagram of an example of a mechanical metamaterial region of a brace according to various embodiments.

FIG. 10 shows a schematic diagram of an example of a mechanical metamaterial region 1010 of a brace according to various embodiments. As shown, according to various embodiments, the mechanical metamaterial region 1010 may include a mesh structure 1012. According to various embodiments, the mesh structure 1012 of the mechanical metamaterial region 1010 may include a plurality of links 1014 and nodes 1016 forming repeating shapes. According to various embodiments, as shown, the repeating shapes may include repeating curvilinear shapes, wherein each of the plurality of links 1014 may be a curved link. According to various embodiments, the mesh structure 1012 may be a network or an arrangement of links 1014 connected at respective nodes 1016 in a manner such that each unit cell of the mesh structure 1012, which is defined by a series of links 1014 forming a closed loop, is of a closed shape. According to various embodiments, the series of links 1014 forming respective unit cell of the mesh structure 1012 may enclose or surround a space. As shown, according to various embodiments, the curvilinear shape may include an ellipse or an oval. According to various embodiments, each of the plurality of links 1014 may include, but not limited to, a curve strut, a curve rod, or a curve post.

The following examples pertain to various embodiments.

Example 1 is a brace for a body joint between at least two portions of a body, the brace including:
at least two anchor regions, wherein a first of the at least two anchor regions is configured to hold the brace to a first of the at least two portions of the body, and a second of the at least two anchor regions is configured to hold the brace to a second of the at least two portions of the body; and
a mechanical metamaterial region between the at least two anchor regions, the mechanical metamaterial region comprising a mesh structure configured to have a two-stage elastic deformation profile along a main tension direction, the two-stage elastic deformation profile comprising a first stage which crossover to a second stage at a predetermined strain threshold of the mesh structure, wherein the first stage of the elastic deformation profile is of a higher compliance than the second stage of the elastic deformation profile.

In Example 2, the subject matter of Example 1 may optionally include that the mesh structure may include a plurality of links and nodes forming repeating shapes,
wherein each node fixedly connects two or more links, and wherein each link is configured to be capable of flexing elastically about respective node and deforming elastically in respective axial direction,
wherein, in the first stage, the plurality of links are elastically flex about corresponding nodes in a manner which transversely compresses the repeating shapes with respect to the main tension direction and lengthen the repeating shapes in the main tension direction so as to provide the first stage of elastic deformation of the mesh structure in the main tension direction, and
wherein, in the second stage, the plurality of links are elastically deformed axially in a manner which stretches the repeating shapes in the main tension direction so as to provide the second stage of elastic deformation of the mesh structure in the main tension direction In Example 3, the subject matter of Example 2 may optionally include that the repeating shapes may include repeating polygon shapes, and wherein each of the plurality of links may include a straight link.

In Example 4, the subject matter of Example 2 may optionally include that the repeating shapes may include repeating curvilinear shapes, and wherein each of the plurality of links may include a curved link In Example 5, the subject matter of any one of Examples 2 to 4 may optionally include that the mesh structure may be a multi-layered structure with links oriented in a same direction formed in a same layer.

In Example 6, the subject matter of any one of Examples 2 to 5 may optionally include that the repeating shapes may include repeating asymmetrical shapes.

In Example 7, the subject matter of any one of Examples 2 to 6 may optionally include that the mechanical metamaterial region may include one or more secondary mesh structures arranged in series or in parallel with respect to the mesh structure, at least one of the one or more secondary mesh structure having a plurality of secondary links and secondary nodes forming repeating secondary shapes, wherein the repeating secondary shapes of the at least one of the one or more secondary mesh structures may be different from the repeating shapes of the mesh structure.

In Example 8, the subject matter of Example 7 may optionally include that the repeating secondary shapes of the at least one or more secondary mesh structures may differ from the repeating shapes of the mesh structure in terms of any one or a combination of orientation, shapes, dimensions or link's thickness.

In Example 9, the subject matter of Examples 7 or 8 may optionally include that the mesh structure and the at least one of the one or more secondary mesh structures may be made of similar or dissimilar materials.

In Example 10, the subject matter of any one of Examples 7 to 9 may optionally include that the at least one or more secondary mesh structures may be a multi-layered structure with links oriented in a same direction formed in a same layer.

In Example 11, the subject matter of any one of Examples 7 to 10 may optionally include that the repeating secondary shapes may include repeating asymmetrical shapes.

In Example 12, the subject matter of any one of Examples 1 to 11 may optionally include a fabric forming a base of at least a part of or the entire brace on which the mesh structure of the mechanical metamaterial region may be attached.

In Example 13, the subject matter of any one of Examples 1 to 12 may optionally include that the mechanical metamaterial region may be formed by additive manufacturing.

Example 14 is a method of manufacturing a brace for a body joint between at least two portions of a body, the method including:
  generating a three dimensional model of the body joint and the at least two portions of the body;
  determining a functional range of motion of the body joint and a upper limit of the functional range of motion of the body joint based on motion measurement or motion analysis of the three dimensional model of the body joint and the at least two portions of the body;
  configuring a three dimensional model of the brace as claimed in any one of claims 1 to 13 in a manner so as to match the predetermined strain threshold of the mesh structure of the mechanical metamaterial region to the upper limit of the functional range of motion of the body joint such that the mesh structure is operating in the first stage of elastic deformation of the mesh structure within the functional range of motion of the body joint and the mesh structure is operating in the second stage of elastic deformation of the mesh structure beyond the upper limit of the functional range of motion of the body joint;
  fabricating the brace via additive manufacturing based on the configured three dimensional model of the brace.

In Example 15, the subject matter of Example 14 may optionally include that fabricating the brace via additive manufacturing may include constructing a physical three dimensional model of the body joint and the at least two portions of the body, and performing additive manufacturing on the physical three dimensional model of the body joint and the at least two portions of the body to fabricate the brace.

In Example 16, the subject matter of Example 14 or 15 may optionally include providing a piece of fabric to form a base for fabricating the brace via additive manufacturing.

In Example 17, the subject matter of any one of Examples 14 to 16 may optionally include that configuring the three dimensional model of the brace may include identifying the at least two anchor regions and the mechanical metamaterial region of the brace with reference to the three dimensional model of the body joint and the at least two portions of the body.

In Example 18, the subject matter of any one of Examples 14 to 17 may optionally include that configuring the three dimensional model of the brace may include selecting a shape, selecting a dimension of the shape, orientating the shape with respect to the main tension direction, and positioning the mechanical metamaterial region of the brace.

In Example 19, the subject matter of any one of Examples 14 to 18 may optionally include that additive manufacturing may include three dimensional (3D) printing.

In Example 20, the subject matter of any one of Examples 14 to 19 may optionally include obtaining data of the body joint and the at least two portions of the body prior to generating the three dimensional model of the body joint and the at least two portions of the body.

Various embodiments have provided a more effective brace for protecting and/or supporting a body joint which may allow movement of the joint within the normal functional range of movement and which may prohibit or restrict movement of the joint beyond the normal functional rage of movement to avoid injury to the joint. Various embodiments have provided a method of manufacturing a customized brace for protecting and/or supporting a body joint.

While the invention has been particularly shown and described with reference to specific embodiments, it should be understood by those skilled in the art that various changes, modification, variation in form and detail may be made therein without departing from the scope of the invention as defined by the appended claims. The scope of the invention is thus indicated by the appended claims and all changes which come within the meaning and range of equivalency of the claims are therefore intended to be embraced.

The invention claimed is:

1. A brace for a body joint between at least two portions of a body, the brace comprising:
  at least two anchor regions, wherein a first of the at least two anchor regions is configured to hold the brace to a first of the at least two portions of the body, and a second of the at least two anchor regions is configured to hold the brace to a second of the at least two portions of the body; and
  a mechanical metamaterial region between the at least two anchor regions, the mechanical metamaterial region comprising a mesh structure, the mesh structure comprising a plurality of links and nodes forming repeating shapes, the plurality of links and nodes being integrally printed to form the mechanical metamaterial region as a one-piece structure, wherein each node fixedly connects two or more links, wherein each node is a point which the two or more links are fixed to each other at the point, wherein the mechanical metamaterial is configured to have a two-stage elastic deformation profile along a main tension direction, the two-stage elastic deformation profile comprising a first stage which crossover to a second stage at a predetermined strain threshold of the mesh structure, wherein the first stage of the elastic deformation profile is of a higher compliance than the second stage of the elastic deformation profile, wherein the predetermined strain threshold of the mesh structure of the mechanical metamaterial region matches an upper limit of a functional range of motion of the body joint such that the mesh structure is operating in the first stage of the two-stage elastic deformation profile within the functional range of motion of the body joint and the mesh structure is operating in the second stage of the two-stage elastic deformation profile beyond the upper limit of the functional range of motion of the body joint.

2. The brace as claimed in claim 1, wherein each link is configured to be capable of flexing elastically about respective node and deforming elastically in respective axial direction, wherein, in the first stage, the plurality of links are elastically flexed about corresponding nodes in a manner which transversely compresses the repeating shapes with respect to the main tension direction and lengthen the repeating shapes in the main tension direction so as to provide the first stage of elastic deformation of the mesh structure in the main tension direction, and wherein, in the second stage, the plurality of links are elastically deformed axially in a manner which stretches the repeating shapes in the main tension direction so as to provide the second stage of elastic deformation of the mesh structure in the main tension direction.

3. The brace as claimed in claim 2, wherein the repeating shapes comprises repeating polygon shapes, and wherein each of the plurality of links comprises a straight link.

4. The brace as claimed in claim 2, wherein the repeating shapes comprises repeating curvilinear shapes, and wherein each of the plurality of links comprises a curved link.

5. The brace as claimed in claim 2, wherein the mesh structure is a multi-layered structure with links oriented in a same direction formed in a same layer.

6. The brace as claimed in claim 2, wherein the repeating shapes comprise repeating asymmetrical shapes.

7. The brace as claimed in claim 2, wherein the mechanical metamaterial region comprises one or more secondary mesh structures arranged in series or in parallel with respect to the mesh structure, at least one of the one or more secondary mesh structures having a plurality of secondary links and secondary nodes forming repeating secondary shapes, wherein the repeating secondary shapes of the at least one of the one or more secondary mesh structures is different from the repeating shapes of the mesh structure.

8. The brace as claimed in claim 7, wherein the repeating secondary shapes of the at least one of the one or more secondary mesh structures differ from the repeating shapes of the mesh structure in terms of any one or a combination of orientation, shapes, dimensions or link's thickness.

9. The brace as claimed in claim 7, wherein the mesh structure and the at least one of the one or more secondary mesh structures may be made of similar or dissimilar materials.

10. The brace as claimed in claim 7, wherein the at least one of the one or more secondary mesh structures is a multi-layered structure with links oriented in a same direction formed in a same layer.

11. The brace as claimed in claim 7, wherein the repeating secondary shapes comprises repeating asymmetrical shapes.

12. The brace as claimed in claim 1, further comprising a fabric forming a base of at least a part of or the entire brace on which the mesh structure of the mechanical metamaterial region is attached.

13. The brace as claimed in claim 1, wherein the mechanical metamaterial region is formed by additive manufacturing.

14. A method of manufacturing a brace for a body joint between at least two portions of a body, the method comprising:

generating a three dimensional model of the body joint and the at least two portions of the body;

determining a functional range of motion of the body joint and a upper limit of the functional range of motion of the body joint based on motion measurement or motion analysis of the three dimensional model of the body joint and the at least two portions of the body;

configuring a three dimensional model of a brace in a manner so as to match a predetermined strain threshold of a mesh structure of a mechanical metamaterial region of the mesh to the upper limit of the functional range of motion of the body joint such that the mesh structure is operating in a first stage of elastic deformation of the mesh structure within the functional range of motion of the body joint and the mesh structure is operating in a second stage of elastic deformation of the mesh structure beyond the upper limit of the functional range of motion of the body joint, wherein the brace comprises, at least two anchor regions, wherein a first of the at least two anchor regions is configured to hold the brace to a first of the at least two portions of the body, and a second of the at least two anchor regions is configured to hold the brace to a second of the at least two portions of the body; and the mechanical metamaterial region between the at least two anchor regions, the mechanical metamaterial region comprising the mesh structure, the mesh structure comprising a plurality of links and nodes forming repeating shapes, wherein each node fixedly connects two or more links, wherein each node is a point which the two or more links are fixed to each other at the point, wherein the mechanical metamaterial is configured to have a two-stage elastic deformation profile along a main tension direction, the two-stage elastic deformation profile comprising the first stage which crossover to the second stage at the predetermined strain threshold of the mesh structure, wherein the first stage of the elastic deformation profile is of a higher compliance than the second stage of the elastic deformation profile; and fabricating the brace via additive manufacturing based on the configured three dimensional model of the brace, wherein the plurality of links and nodes of the mesh structure are integrally printed to form the mechanical metamaterial region as a one-piece structure.

15. The method as claimed in claim 14, wherein fabricating the brace via additive manufacturing comprises constructing a physical three dimensional model of the body joint and the at least two portions of the body, and performing additive manufacturing on the physical three dimensional model of the body joint and the at least two portions of the body to fabricate the brace.

16. The method as claimed in claim 14, further comprising providing a piece of fabric to form a base for fabricating the brace via additive manufacturing.

17. The method as claimed in claim 14, wherein configuring the three dimensional model of the brace comprises identifying the at least two anchor regions and the mechanical metamaterial region of the brace with reference to the three dimensional model of the body joint and the at least two portions of the body.

18. The method as claimed in claim 14, wherein configuring the three dimensional model of the brace comprises selecting a shape, selecting a dimension of the shape, orientating the shape with respect to the main tension direction, and positioning the mechanical metamaterial region of the brace.

19. The method as claimed in claim 14, wherein additive manufacturing comprises three dimensional (3D) printing.

20. The method as claimed in claim 14, further comprising obtaining data of the body joint and the at least two portions of the body prior to generating the three dimensional model of the body joint and the at least two portions of the body.

* * * * *